US010787709B2

(12) United States Patent
Murphy et al.

(10) Patent No.: US 10,787,709 B2
(45) Date of Patent: *Sep. 29, 2020

(54) METHODS FOR DIAGNOSING RISK OF RENAL ALLOGRAFT FIBROSIS AND REJECTION

(71) Applicant: Icahn School of Medicine at Mount Sinai, New York, NY (US)

(72) Inventors: Barbara Murphy, Pelham Manor, NY (US); Weijia Zhang, Cresskill, NJ (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/424,014

(22) Filed: May 28, 2019

(65) Prior Publication Data

US 2019/0345556 A1 Nov. 14, 2019

Related U.S. Application Data

(63) Continuation of application No. 15/320,208, filed as application No. PCT/US2015/038147 on Jun. 26, 2015, now Pat. No. 10,308,985.

(60) Provisional application No. 62/017,803, filed on Jun. 26, 2014.

(51) Int. Cl.
| | | |
|---|---|---|
| C07H 21/04 | (2006.01) | |
| *C12Q 1/6883* | (2018.01) | |
| A61K 38/18 | (2006.01) | |
| A61K 38/17 | (2006.01) | |
| A61K 38/13 | (2006.01) | |
| A61K 31/573 | (2006.01) | |
| A61K 31/5377 | (2006.01) | |
| A61K 31/52 | (2006.01) | |
| A61K 38/22 | (2006.01) | |
| C07K 14/705 | (2006.01) | |
| A61K 31/343 | (2006.01) | |
| A61K 31/436 | (2006.01) | |
| A61K 31/4412 | (2006.01) | |

(52) U.S. Cl.
CPC .......... *C12Q 1/6883* (2013.01); *A61K 31/343* (2013.01); *A61K 31/436* (2013.01); *A61K 31/4412* (2013.01); *A61K 31/52* (2013.01); *A61K 31/5377* (2013.01); *A61K 31/573* (2013.01); *A61K 38/13* (2013.01); *A61K 38/1774* (2013.01); *A61K 38/18* (2013.01); *A61K 38/1875* (2013.01); *A61K 38/2221* (2013.01); *C07K 14/70521* (2013.01); *C07K 2319/30* (2013.01); *C12Q 2600/118* (2013.01); *C12Q 2600/158* (2013.01); *C12Q 2600/178* (2013.01); *G01N 2800/245* (2013.01); *G01N 2800/347* (2013.01); *G01N 2800/52* (2013.01)

(58) Field of Classification Search
USPC ...................................................... 536/24.5
See application file for complete search history.

(56) References Cited

U.S. PATENT DOCUMENTS

| | | | |
|---|---|---|---|
| 2006/0270612 | A1 | 11/2006 | Blatt et al. |
| 2011/0144914 | A1* | 6/2011 | Harrington .......... C12Q 1/6883 702/19 |
| 2011/0171664 | A1 | 7/2011 | O'Brien |
| 2014/0100124 | A1 | 4/2014 | Wylie et al. |
| 2014/0141986 | A1 | 5/2014 | Spetzler et al. |

FOREIGN PATENT DOCUMENTS

| | | |
|---|---|---|
| CN | 1518458 A | 8/2004 |
| CN | 102666581 A | 9/2012 |
| CN | 103421905 A | 12/2013 |
| WO | WO 2011/143499 | 11/2011 |
| WO | WO 2013/063322 | 5/2013 |
| WO | WO 2013063544 A | 5/2013 |
| WO | WO 2014/071205 | 5/2014 |

OTHER PUBLICATIONS

Gorantla, Vijay S., et al. "Immunosuppressive agents in transplantation: Mechanisms of action and current anti-rejection strategies." Microsurgery: Official Journal of the International Microsurgical Society and the European Federation of Societies for Microsurgery 20.8 (2000): 420-429.*
Ben-Dov et al., "MicroRNA sequence profiles of human kidney allografts with or without tubulointerstitial fibrosis," *Transplantation.*, 94(11):1086-1094, Dec. 15, 2012.
Cho et al. (2010 Expert Opinion on Investigational Drugs, 19:2, 275-283).
Extended European Search Report in International Application No. EP110466HV, dated Feb. 1, 2018, 10 pages.
Gorantla et al. (Immunosuppressive agents in transplantation: mechanisms of action and current anti-rejection strategies. Microsurgery 20 (2000): 420-429).
International Preliminary Report on Patentability in International Application No. PCT/US2015/038147, dated Dec. 27, 2016, 10 pages.
International Search Report dated Oct. 23, 2015 for PCT/US2015/038147.
Kulkarni, Meghana M. ("Digital multiplexed gene expression analysis using the NanoString nCounter system." Current Protocols in Molecular Biology (2011): 25B-10).
Maluf et al., "The urine microRNA profile may help monitor post-transplant renal graft function," *Kidney International.*, 85(2):439-449, Jan. 1, 2014.

(Continued)

*Primary Examiner* — Kimberly Chong
(74) *Attorney, Agent, or Firm* — Fish & Richardson P.C.

(57) ABSTRACT

Disclosed herein is a method for diagnosing a renal allograft recipient's risk for developing fibrosis of the allograft and allograft loss. The method includes determining the expression levels of certain microRNAs, which have been determined to be predictive of an allograft recipient's risk. Also disclosed herein is a method of treating a renal allograft recipient to inhibit fibrosis of the allograft and allograft loss, as well as kits for use in the methods disclosed herein.

28 Claims, 12 Drawing Sheets

(56) References Cited

OTHER PUBLICATIONS

Office Action in European Application No. 15811195.5, dated Jul. 9, 2019, 4 pages.
Omran, A et al. MicroRNAs: New Insights into Chronic Childhood Diseases. Jul. 7, 2013. BioMed Research International, vol. 2013, Article ID 291826, 13 pages; Table 1; p. 6, col. 1, p. 5.
Spector, Y et al. Development and Validation of a MicroRNA-Based Diagnostic Assay for Classification of Renal Cell Carcinomas. Molecular Oncology. Mar. 26, 2013, vol. 7, pp. 732-738; p. 734, col. 2, paragraph 1.
Office Action in Chinese Application No. 201580045235.5, dated Jan. 16, 2020, 8 pages (English translation).

* cited by examiner

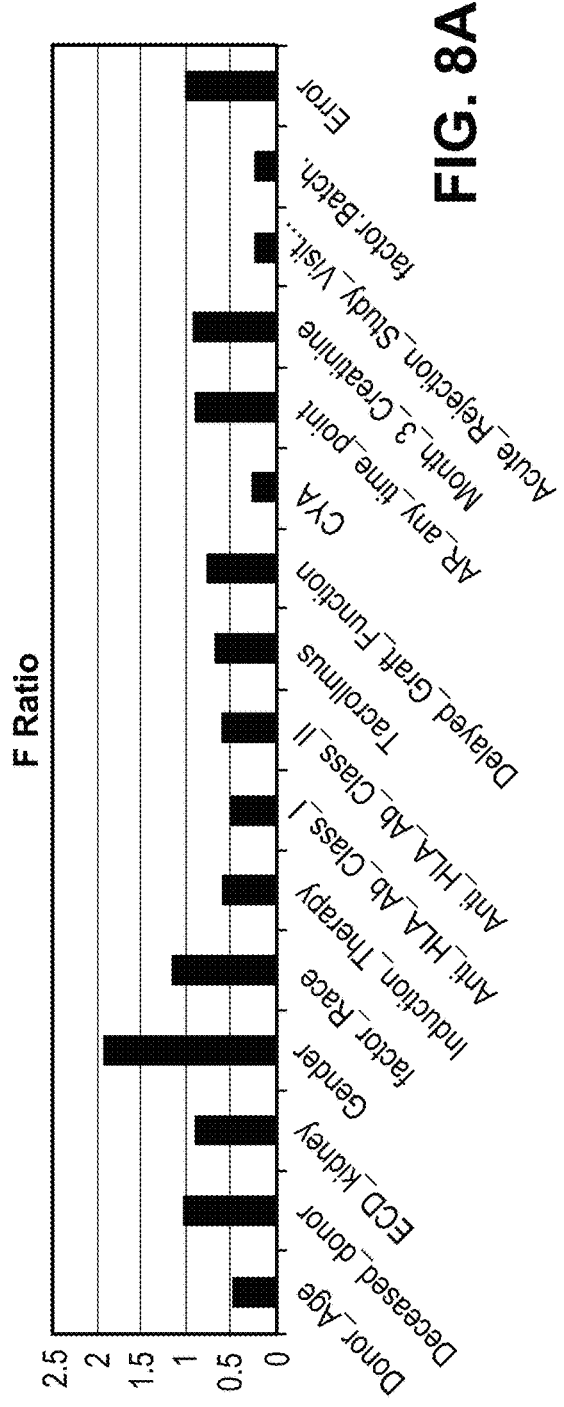
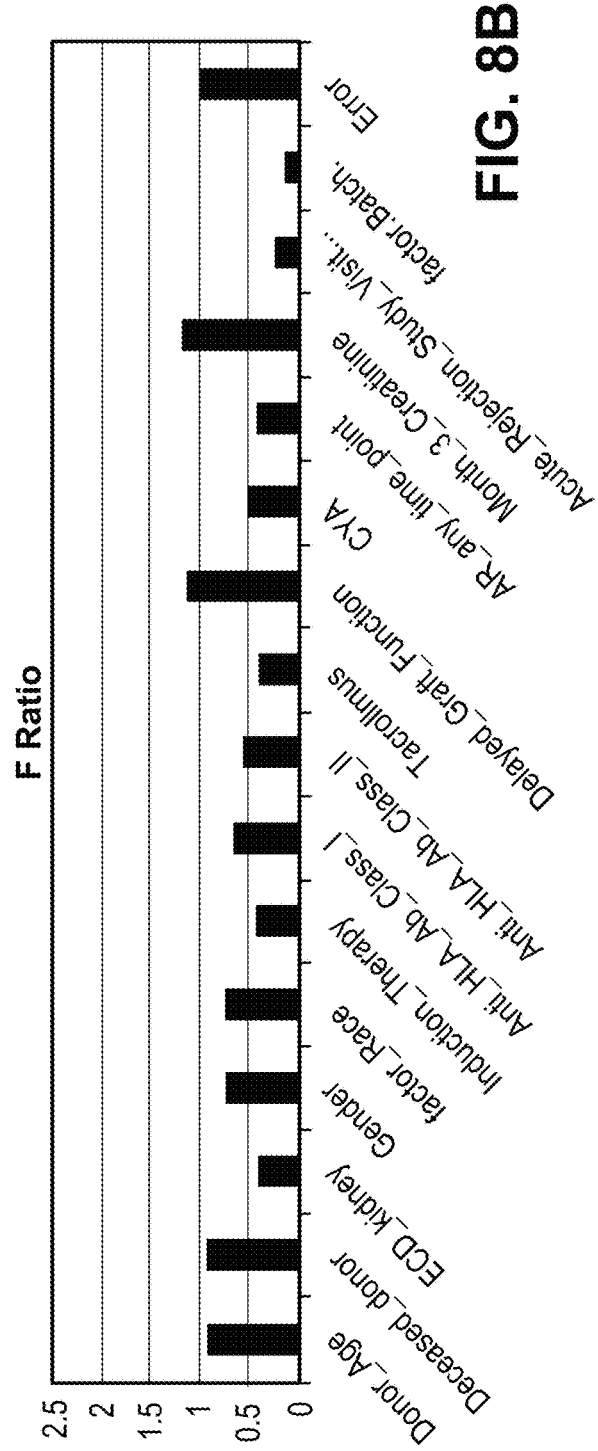

METHODS FOR DIAGNOSING RISK OF RENAL ALLOGRAFT FIBROSIS AND REJECTION

CROSS-REFERENCE TO RELATED APPLICATIONS

This application claims the benefit of U.S. Application No. 62/017,803, filed on Jun. 26, 2014, which is incorporated by reference herein in its entirety.

GOVERNMENT GRANT CLAUSE

This invention was made with government support under grant no. 1U01AI070107-01 awarded by the National Institutes of Health. The government has certain rights in the invention.

TECHNICAL FIELD

This invention relates to the field of molecular biology, and more particularly to detecting microRNA molecular signatures. More particularly, this invention relates to methods for diagnosing a renal allograft recipient's risk for developing fibrosis of the allograft and allograft loss. The methods comprise analyzing the blood of renal allograft recipients by determining the expression level of a miRNA signature set containing at least 4 preselected miRNA in order to identify and treat such patients. A logistic regression fitting model can be applied to normalized expression read count (e.g. read counts of genes from next generation sequencing technology) values to derive a statistical model from which a probability score for risk of fibrosis of the allograft and allograft loss can be calculated for each patient.

BACKGROUND

Progressive renal fibrosis leading to decline in renal function remains the predominant cause of renal allograft loss. Current methodologies based on clinical and pathological parameters fail to identify grafts at risk for loss prior to the development of irreversible injury. Such tests usually require obtaining a biopsy specimen from the patient. Often by the time rejection is recognized it is too late to do anything. An increase in serum creatinine or an increase of protein in the urine may be warnings of rejection but are not entirely predictive. Furthermore, the collection and assaying of patient biopsy samples is time-consuming and expensive.

Thus, there remains a need for improved diagnostic methods for predicting a renal allograft recipient's risk for developing fibrosis of the allograft and allograft loss.

SUMMARY

Disclosed herein is a method for diagnosing a renal allograft recipient's risk for developing fibrosis of the allograft and allograft loss. The method generally includes measuring the level of a miRNA signature in a test sample (e.g., a blood specimen) from the recipient. The signature comprises the determination of an alteration in levels of miRNA signature in a test sample from an allograft recipient. In some embodiments, the miRNA signature consists of miRNA gene products: hsa-mir-128, hsa-mir-29b-3p, hsa-mir-302b-3p, and hsa-mir-192-5p. An alteration in the levels of the miRNA, relative to the level of corresponding levels of miRNA in a control sample is indicative of the allograft recipient's risk of developing fibrosis of the allograft and allograft loss.

In some aspects, the disclosure provides methods for determining a renal allograft recipient's (e.g., a "recipient," a "renal allograft patient," or "a patient) risk of developing fibrosis of the allograft and/or allograft loss, comprising comparing the expression levels of the four microRNAs with a control level for each microRNA, wherein the microRNAs are hsa-mir-128, hsa-mir-29b-3p, hsa-mir-302b-3p, and hsa-mir-192-5p; and (i) diagnosing the recipient as being at high risk for developing fibrosis of the allograft and allograft loss if the expression levels of hsa-miR-128 and hsa-miR-302b-3p are increased relative to a control level for each microRNA, and the expression levels of hsa-miR-29b-3p and hsa-miR-192-5p are decreased relative to the control level for each microRNA based on the probability score cutoff determined from the training set; or (ii) diagnosing the recipient as being at low risk for developing fibrosis of the allograft and allograft loss if the expression levels of hsa-miR-128 and hsa-miR-302b-3p are decreased relative to the control level for each microRNA, and the expression levels of hsa-miR-29b-3p and hsa-miR-192-5p are increased relative to the control level for each microRNA based on the probability score cutoff determined from the training set.

In some aspects, the disclosed methods can included obtaining a blood sample from the recipient; determining the expression levels of four microRNAs in the sample, wherein the microRNAs are hsa-mir-128, hsa-mir-29b-3p, hsa-mir-302b-3p, and hsa-mir-192-5p; comparing the expression levels of the four microRNAs with a control level for each microRNA, and diagnosing the recipient as being risk for developing fibrosis of the allograft and allograft loss if the expression levels of the miRNA samples are altered relative to a control level for each microRNA. Determining the expression levels can include, for example, isolating total mRNA from the blood specimen, synthesizing cDNA from the mRNA, and measuring the expression levels of microRNAs hsa-mir-128, hsa-mir-29b-3p, hsa-mir-302b-3p, and hsa-mir-192-5p from the sample.

In some aspects, the disclosed methods can include: obtaining a blood specimen from the renal allograft recipient; isolating (i.e., extracting) total mRNA from the blood specimen; synthesizing cDNA from the mRNA; determining the expression levels of four microRNAs, wherein the microRNAs are hsa-mir-128, hsa-mir-29b-3p, hsa-mir-302b-3p, and hsa-mir-192-5p; comparing the expression levels of each of the microRNA's to a predetermined control level, and diagnosing the allograft recipient as: (i) at high risk for developing fibrosis of the allograft and allograft loss if the expression levels of hsa-miR-128 and hsa-miR-302b-3p are increased relative to the control level for each microRNA, and the expression levels of hsa-miR-29b-3p and hsa-miR-192-5p are decreased relative to the control level for each microRNA based on the probability score cutoff determined from the training set; or (ii) at low risk for developing fibrosis of the allograft and allograft loss if the expression levels of hsa-miR-128 and hsa-miR-302b-3p are decreased relative to the control level for each microRNA, and the expression levels of hsa-miR-29b-3p and hsa-miR-192-5p are increased relative to the control level for each microRNA based on the probability score cutoff determined from the training set.

In some aspects of the method, a high risk for developing fibrosis of the allograft and allograft loss corresponds to a 12-month Chronic Allograft Damage Index CADI-12 of score of 1 or greater. The CADI score is based on individual component scores for a) diffuse or focal inflammation, b) fibrosis in the interstitium, c) increase in mesangial matrix, d) sclerosis in glomeruli, e) intimal proliferation, and f) tubular atrophy. Each individual parameter is scored from 0 to 3 as described in the literature (Yilmaz et al., 2003, Journal of the American Society of Nephrology: JASN. 14:773-779). In some aspects of the method, a low risk for developing fibrosis of the allograft and allograft loss corresponds to a CADI-12-score of less than 1.

In some aspects of the method, the method further comprises performing a comparison between the measured expression levels of the miRNA in the recipient's sample with one or more reference (i.e., control) samples, said references being representative of healthy human subjects.

In some aspects, diagnosing the recipient's risk comprises calculating the recipient's risk by applying the expression levels determined in the recipient's sample to a penalized logistic regression fitting model. In one embodiment, the penalized to logistic regression fitting model from which the risk will be calculated utilizes the formula:

$$\log\frac{p(x)}{1-p(x)} = \beta^*_{0+}\beta^*_1 g_1 + \beta^*_i g_i + \ldots + \beta^*_4 g_4$$

where (p(x) is the probability of developing fibrosis, $\beta^*_i$ is penalized coefficiency and $g_i$ is the expression value of miRNA i.

In some aspects, diagnosing the recipient's risk comprises calculating the probability score of fibrosis risk for said recipient using the equation:

$$\log\frac{p(x)}{1-p(x)} = \beta^*_{0+}\beta^*_1 g_1 + \beta^*_i g_i + \ldots + \beta^*_4 g_4$$

where (p(x) is the probability of developing fibrosis, $\beta^*_i$ is penalized coefficiency and $g_i$ is the expression value of miRNA i. In certain embodiments, the method further comprises designing a treatment plan based on the diagnosis.

In certain embodiments, the method further comprises administration of a treatment based on the diagnosis.

In some aspects of the method, the method further includes treating the allograft recipient to inhibit fibrosis of the allograft and allograft loss if the allograft recipient has been diagnosed as being at risk for fibrosis of the allograft and allograft loss. Thus, in some aspects, the method comprises administering an anti-fibrosis drug to the allograft recipient.

Thus, also disclosed herein is a method for treating a renal allograft recipient to inhibit fibrosis of the allograft and allograft loss. The method can include obtaining a blood specimen from the renal allograft recipient; isolating miRNA from the blood specimen; synthesizing cDNA from the miRNA; determining the expression levels of four microRNAs, wherein the microRNAs are hsa-mir-128, hsa-mir-29b-3p, hsa-mir-302b-3p, and hsa-mir-192-5p; comparing the expression level of each of the microRNAs to a control level for each micoRNA; diagnosing the allograft recipient as: (i) at high risk for developing fibrosis of the allograft and allograft loss if the expression levels of hsa-miR-128 and hsa-miR-302b-3p are increased relative to the control level for each microRNA, and the expression levels of hsa-miR-29b-3p and hsa-miR-192-5p are decreased relative to the control level for each microRNA based on the probability score cutoff determined from the training set; or (ii) at low risk for developing fibrosis of the allograft and allograft loss if the expression levels of hsa-miR-128 and hsa-miR-302b-3p are decreased relative to the control level for each microRNA, and the expression levels of hsa-miR-29b-3p and hsa-miR-192-5p are increased relative to the control level for each microRNA based on the probability score cutoff determined from the training set, and administering an anti-rejection and/or an anti-fibrosis drug to the allograft recipient and/or modifying their immunosuppression regimen if the recipient has expression levels of hsa-miR-128 and hsa-miR-302b-3p that are increased relative to the control level for each microRNA, and the expression levels of hsa-miR-29b-3p and hsa-miR-192-5p are decreased relative to the control level for each microRNA.

In some aspects of the treatment methods disclosed herein, the treatment includes administering the allograft recipient an anti-rejection drug to the allograft recipient. In some aspects, the anti-rejection drug is Belatacept (a fusion protein composed of the Fc fragment of a human IgG1 immunoglobulin linked to the extracellular domain of CTLA-4). In some aspects, the anti-rejection drug is an immunosuppressive or anti-proliferative agent, mycophenolate mofetil (MMF), sirolimus, prednisone, Mycophenolate Mofetil, Mycophenolate Sodium and Azathioprine.

In some aspects of the treatment methods disclosed herein, the treatment includes administering an anti-fibrosis (e.g., anti-fibrotic) drug to the allograft recipient. In some aspects, the anti-fibrosis drug is selected from the group consisting of Pirfenidone, relaxin, Bone morphogenetic protein 7 (BMP-7) and Hepatic growth factor (HGF) 6. In some aspects of the treatment methods disclosed herein, the treatment method includes modifying the allograft recipient's immunosuppression regimen by, for example, switching from a calcineurin inhibitor to a drug which is not associated with the development of fibrosis such as the anti-rejection drugs Belatacept, rapamycin or Mycophenolate Mofetil.

In some aspects of the method, determining the expression levels hsa-mir-128, hsa-mir-29b-3p, hsa-mir-302b-3p, and hsa-mir-192-5p includes performing an assay such as qPCR, microarray, or Nanostring analysis. For Nanostring analysis, the analysis includes annealing total RNA comprising the miRNAs to barcode probes specific for the microRNAs, immobilizing the miRNA, and quantifying the probes bound to the miRNA by digital analyzer.

In another aspect, there is provided herein a DNA chip for diagnosing a renal allograft recipient's risk for developing fibrosis of the allograft and allograft loss, on which a probe has been immobilized to assay the expression levels of hsa-mir-128, hsa-mir-29b-3p, hsa-mir-302b-3p, and hsa-mir-192-5p.

In some aspects, the disclose provides methods for selecting a renal allograft patient for treatment for reducing fibrosis of the allograft, and for treatment to reduce the risk of allograft loss, the methods comprising comparing the expression levels of the four microRNAs with a control level for each microRNA, wherein the microRNAs are hsa-mir-128, hsa-mir-29b-3p, hsa-mir-302b-3p, and hsa-mir-192-5p, and (0 selecting the patient for treatment if a the expression levels of hsa-miR-128 and hsa-miR-302b-3p are increased relative to a control level for each microRNA, and the expression levels of hsa-miR-29b-3p and hsa-miR-192-5p are decreased relative to the control level for each microRNA. According to some aspects, the methods can include obtaining a blood sample from the recipient, determining the expression levels of four microRNAs in the sample, wherein the microRNAs are hsa-mir-128, hsa-mir-29b-3p, hsa-mir-302b-3p, and hsa-mir-192-5p, comparing the expression levels of the four microRNA's with a control level for each microRNA, and selecting the patient for treatment if a the expression levels of the miRNA samples are altered relative to a control level for each microRNA In some embodiments, the patient is selecting for treatment if a the expression levels of hsa-miR-128 and hsa-miR-302b-3p are increased relative to a control level for each microRNA, and the expression levels of hsa-miR-29b-3p and hsa-miR-192-5p are decreased relative to the control level for each microRNA.

The present disclosure also provides a kit for determining a renal allograft recipient's risk of developing fibrosis of the allograft and allograft loss. The kits include reagents suitable for determining expression levels of a miRNA in a blood sample (e.g., reagents suitable for determining expression levels of hsa-mir-128, hsa-mir-29b-3p, hsa-mir-302b-3p, and hsa-mir-192-5p); optionally one or more control samples comprising predetermined levels of the same miRNA, wherein comparison of the levels of the miRNAs in a test sample with levels in the control samples identifies a renal allograft recipient's risk for developing fibrosis of the allograft and allograft loss; and instructions for use of the kit in the method described herein. In some embodiments, the kit comprises one or more barcode probes that specifically hybridize to one or more of (e.g., one or more, two or more, three or more, or all of four of) hsa-mir-128, hsa-mir-29b-3p, hsa-mir-302b-3p, and hsa-mir-192-5p. In some aspects, the kit further includes one or more microRNA extraction reagents. In some aspects, the kit further includes an annealing reagent. In some aspects, the kit further includes instructions for use.

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

In some embodiments, the reference sample is obtained from at least one individual who is not the recipient of a renal allograft. In some other embodiments, the reference sample is obtained from at least one renal allograft recipient previously diagnosed as having being at risk for developing fibrosis of the allograft and allograft loss. In some embodiments, the reference sample comprises a predetermined, statistically significant reference analyte level (e.g. predetermined, statistically significant reference miRNA expression levels).

In yet another embodiment, the methods further comprise modifying the allograft recipient's clinical record to identify the recipient as being at risk for developing fibrosis of the allograft and allograft loss. Preferably, the clinical record is stored in a computer readable medium.

The details of one or more embodiments of the invention are set forth in the accompanying drawings and the description below. Other features, objects, and advantages of the invention will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 3.

FIG. 4.

FIG. 8 shows two quantifying F ratio, and show the clinical or demographic sources contributing to data variation before (FIG. 8a) and after (FIG. 8b) SVA correction.

DETAILED DESCRIPTION

Overview

Figure 1:
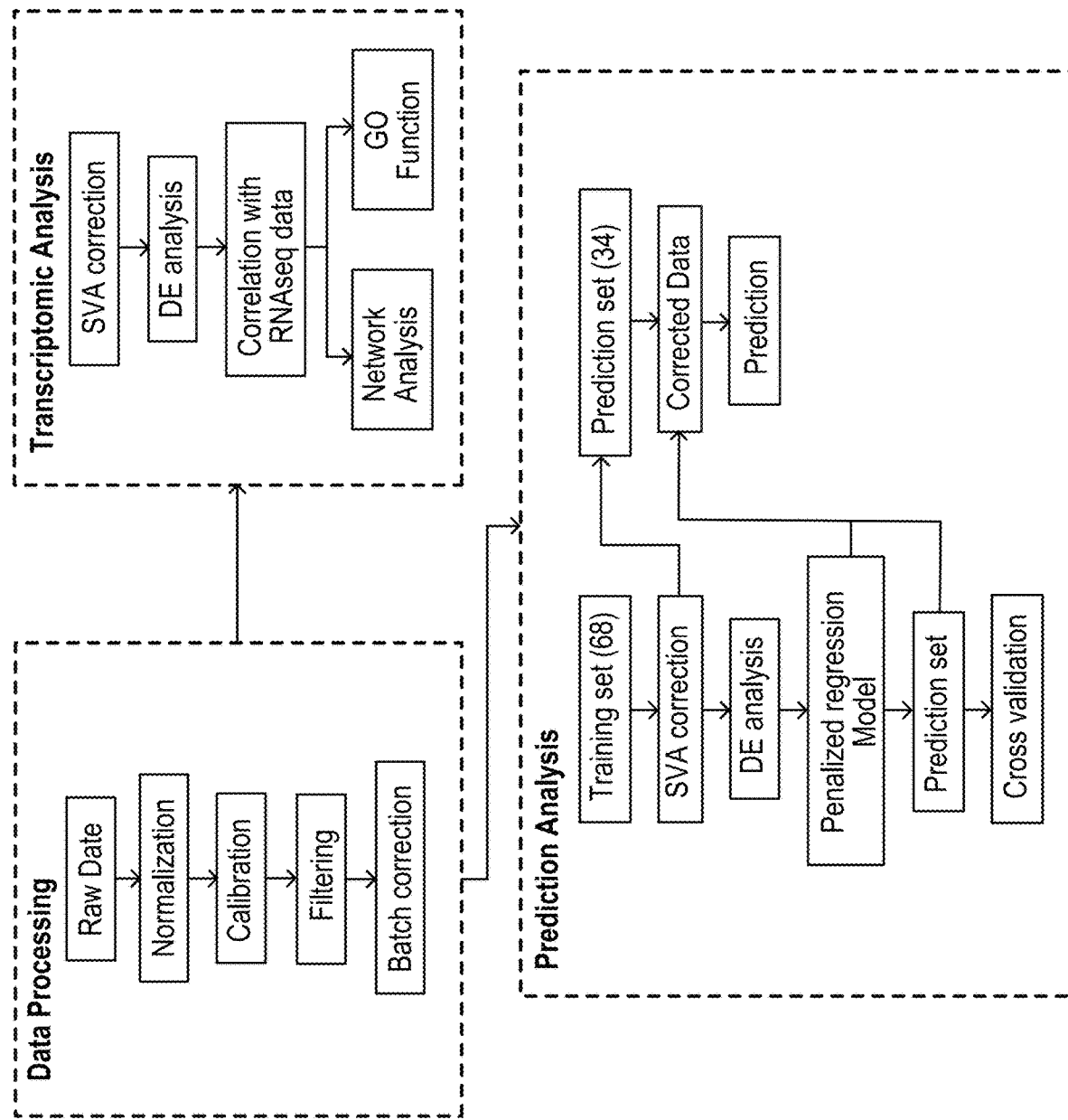
FIG. 1. depicts a data analysis workflow.

The present disclosure is directed to methods for diagnosing a renal allograft recipient's risk for developing fibrosis of the allograft and allograft loss. Fibrosis can result in loss of the allograft. The methods described herein are useful for identifying whether a renal allograft recipient is at risk for developing fibrosis of the allograft and allograft loss. Stated another way, the methods described herein are useful for determining the probability a renal allograft recipient is at risk for developing fibrosis of the allograft and allograft loss, the methods relying on differences in the relative amounts (e.g., expression level) of miRNA obtained from the recipient, wherein the probability is determined using a linear regression model as described herein.

The assay technique disclosed herein is a blood-based assay that avoids the need for biopsy specimens. Allograft recipients can be monitored using the assays disclosed herein at the time of transplant, early post-transplant and periodically thereafter. If an allograft recipient is determined to be at high risk for developing fibrosis of the allograft and for allograft loss, the allograft recipient can be treated, e.g., through modification of the allograft recipient's immunosuppression regimen, such as, for example administering, discontinuing administration or adjusting dosage on an immunosuppressive medication (e.g., anti-rejection medications), or by administering one or more anti-fibrosis agents.

As described in the Examples, below, a molecular signature to predict development/progression of renal allograft fibrosis was discovered. The data demonstrated the use of peripheral miRNA profiling for surveillance and to stratify patients at risk for fibrosis and graft loss, obviating the need for allograft biopsy, and identifying those who may benefit from early interventions to prevent chronic allograft loss.

The assay technique disclosed herein addresses to need for improved diagnostic methods for predicting a renal allograft recipient's risk for developing fibrosis of the allograft and allograft loss, and provides a blood based assay that is easily administered repetitively to transplant patients. Renal transplant patients are examined by their physician very frequently post transplantation—in most instances twice per week for the first month moving to weekly and then every other week getting to monthly after 4 to 5 months, with time intervals between visits gradually increasing thereafter. During this time, the patients' renal function and the immunosuppression levels are monitored. Steroids are typically tapered to 5 mg by 3 months post-surgery and the tacrolimus (a drug that suppresses the immune system and is used to prevent rejection of transplanted organs) levels are gradually reduced to a steady level by 6-12 months if the post-transplant course has no complications and the patient is not high immunological risk. The miRNA expression profiles described below can be employed as a standard test to be performed at the time of a clinical visit. A positive test result (i.e. if the expression levels of the miRNA samples are altered relative to a control level for each microRNA) indicates that the for developing fibrosis of the allograft and allograft loss, and would be treated by increasing modifying the patient's immunosuppressive dosing regimen and by administering anti-fibrosis drugs. Repeat testing (which can be done economically since the assay is preferably a blood based test) will guide the continued modifications, if any, to the patient's immunosuppressive dosing regimen.

In the Examples, miRNA profiling was performed using Nanostring technology on peripheral blood at 3-months post-transplant from a cohort of 102 kidney transplant patients from the Genomics of Chronic Allograft Rejection (GoCAR) study. LIMMA analysis of miRNA expression profiles identified a set of 24 miRNAs significantly associated with a high 12-month CADI score (e.g., a CADI-12 score of >1). Correlation of miRNA expression profiles with RNAseq gene expression profiles on the same patients (N=96) identified negatively correlated miRNA predicted targets and Gene Ontology enrichment further predicted the biological processes miRNAs might take part in. The mir-128, which is known to play roles in tumorigenesis, was the most significantly upregulated in high CADI patients, and associated with genes in immune response and cell proliferation and apoptosis. The mir-29b-3p was the most downregulated in high CADI (e.g., CADI-12 score of >1) patients and associated with genes in transcription regulation, DNA repair pathways through in ATM pathway.

miRNA profiling identified a miRNA set for prediction of development of renal allograft fibrosis and allograft loss. It was discovered, in particular, that the four microRNAs, hsa-mir-128, hsa-mir-29b-3p, hsa-mir-302b-3p, and hsa-mir-192-5p, can be used together to diagnose an allograft recipient's risk for developing fibrosis of the allograft and allograft loss with a high predictive value. In allograft recipients who had a high CADI (e.g., CADI-12 score of >1), hsa-miR-128, hsa-miR-182-5p, hsa-miR-151a-5p, hsa-miR-30c-5p, hsa-miR-302b-3p, hsa-miR-378e, hsa-miR-30b-5p, hsa-miR-23b-3p, hsa-miR-423-5p, hsa-miR-26a-5p, hsa-miR-423-5p, hsa-miR-26a-5p, hsa-miR-186-5p, hsa-miR-361-5p, and hsa-miR-22-3p were upregulated; and the miRNAs, hsa-miR-7b-5p, hsa-miR-1991-5p, hsa-miR-22-3p, hsa-miR-7b-5p, hsa-miR-199a-5p, hsa-miR-7g-5p, hsa-miR-192-5p, hsa-miR-106b-5p, hsa-miR-15a-5p, hsa-miR-374a-5p, hsa-miR-126-3p, hsa-miR-29c-3p, hsa-miR-1226-3p, and hsa-miR-29b-3p were downregulated. Thus, miRNA signatures can be developed based on this data, which identifies a patient as at high risk of developing fibrosis of the allograft and allograft loss. Alternatively, the expression levels of any individual miRNAs can be determined to assess the allograft recipient's risk of fibrosis and allograft loss. Particularly preferred individual miRNAs for use in the present methods for diagnosis and/or treatment include, e.g., miR-128, hsa-miR-302b-3p, hsa-miR-29b-3p and hsa-miR-192-5p.

In certain embodiments, a particular subset of 4 of the above-described miRNAs is highly predictive of an allograft recipient being at high risk for developing fibrosis of the allograft and allograft loss. In particular, an allograft recipient can be diagnosed as at high risk for developing fibrosis of the allograft and allograft loss if the expression levels of hsa-miR-128 and/or hsa-miR-302b-3p are increased relative to a control level for each microRNA, and/or the expression levels of hsa-miR-29b-3p and/or hsa-miR-192-5p are decreased relative to a control level for each microRNA.

In other embodiments, an allograft recipient's expression levels of miR-128, hsa-miR-302b-3p, hsa-miR-29b-3p and hsa-miR-192-5p are compared to a reference value or reference set (control) for the miRNAs, and the relative risk of the allograft recipient is assessed based on statistical analysis.

In other embodiments, an allograft recipient can be diagnosed as at low risk for developing fibrosis of the allograft and allograft loss if the expression levels of hsa-miR-128 and/or hsa-miR-302b-3p are decreased relative to a control level or reference profile for each microRNA, and/or if the expression levels of hsa-miR-29b-3p and/or hsa-miR-192-5p are increased relative to a control level or reference profile for each microRNA.

In other embodiments, the miRNAs are analyzed collectively, and the relative risk for developing fibrosis of the allograft and allograft loss is assessed based on comparing the miRNA profile of the allograft recipient to a reference profile (e.g., derived from or based on the levels of a cohort of allograft recipients who are known to not be at risk for developing fibrosis of an allograft and allograft loss), wherein the comparison includes considering the expression profile of miR-128, hsa-miR-302b-3p, hsa-miR-29b-3p and hsa-miR-192-5p, or a subset thereof.

In some embodiments, the miRNA expression profile can be determined using an nCounter® analysis system (NanoString Technologies®, Seattle, Wash.). The nCounter® Analysis System from NanoString Technologies profile hundreds of mRNAs, microRNAs, or DNA targets simultaneously with high sensitivity and precision. Target molecules are detected digitally. The NanoString analysis system uses molecular "barcodes" and single-molecule imaging to detect and count hundreds of unique transcripts in a single reaction. The protocol does not include any amplification steps. While this is a preferred method for rapid detection of the expression of miRNA, any suitable method for detection known in the art may be used according to the present methods. For example, and without limitation, miRNA can be detected using polymerase chain reaction (PCR), quantitative (q)PCR or micro array.

Definitions

As used herein, an allograft recipient who is at "high risk" of developing fibrosis of the allograft and allograft loss is significantly more likely to develop fibrosis and allograft failure, without intervention, than a subject who is at "low risk."

As used herein, the "expression level" of an miRNA disclosed herein means the mRNA expression level of the marker, or the measurable level of the marker in a sample, which can be determined by any suitable method known in the art, such as, but not limited to Northern blot, polymerase chain reaction (PCR), e.g., quantitative real-time, "QPCR", microarray, and Nanostring analysis, etc.

In some methods herein, it is desirable to detect and quantify miRNAs present in a sample. Detection and quantification of RNA expression can be achieved by any one of a number of methods well known in the art. Using the known sequences for RNA family members, specific probes and primers can be designed for use in the detection methods described below as appropriate.

In some cases, detection and quantification of RNA expression requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miR-NAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs). Extraction procedures such as those using QIAGEN-ALLprep kit are also contemplated.

In some embodiments, use of a microarray is desirable. A microarray is a microscopic, ordered array of nucleic acids, proteins, small molecules, cells or other substances that enables parallel analysis of complex biochemical samples. A DNA microarray has different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarray analysis of miRNAs, for example (although these procedures can be used in modified form for any RNA analysis) can be accomplished according to any method known in the art. In one example, RNA is extracted from a cell or tissue sample, the small RNAs (18-26-nucleotide RNAs) are size-selected from total RNA using denaturing polyacrylamide gel electrophoresis. Oligonucleotide linkers (e.g., barcodes) are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays that can be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about"

means within about a log (i.e., an order of magnitude) preferably within a factor of two of a given value.

As used herein, "determining the level of expression," "determining the expression level" or "detecting the level of express", as in, for example, "determining the expression level of miRNA" refers to quantifying the amount of miRNA present in a sample. Detecting expression of the specific miRNA, or any microRNA, can be achieved using any method known in the art or described herein. Detecting expression of miRNA includes detecting expression of either a mature form of miRNA or a precursor form that is correlated with miRNA expression. Typically, miRNA detection methods involve sequence specific detection, such as by RT-PCR. miRNA-specific primers and probes can be designed using the precursor and mature miRNA nucleic acid sequences, which are known in the art.

As used herein, a "altered" level of expression of a miRNA compared to reference level or control level is an at least 0.5-fold (e.g., at least: 1-2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) altered level of expression of the miRNA. It is understood that the alteration can be an increase or a decrease. Alternatively, altered expression level is defined as an increase in the risk probability score using parameters in the logistic regression model established from a training patient group, comparing the probability score to the cutoff derived from the training set.

The terms "decrease", "decreased", "reduced", "reduction" or "down-regulated" are all used herein generally to mean a decrease by a statistically significant amount. However, for avoidance of doubt, "reduced", "reduction", "down-regulated" "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold (e.g., at least: 1-2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold (e.g., at least: 1-2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) or greater as compared to a reference level.

As used herein, the term "selectively targets", e.g., in the context of a probe for detecting miRNA expression, means the targeting agent binds specifically to the target, and does not bind nonspecifically to other targets.

Throughout the application and in the appended claims, it should be understood and is intended to be understood that use of the terms "drug", "medication", "agent" and "therapeutic agent" are interchangeable expressions defining the same or similar entities. A "drug" refers generally to a chemical compound, small molecule, or other biologic composition, such as an antisense compound, antibody, protease inhibitor, hormone, chemokine or cytokine, capable of inducing a desired therapeutic or prophylactic effect when properly administered to a subject.

As used herein, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition (e.g., fibrosis of a renal allograft and/or allograft loss); and/or (2) inhibiting the state, disorder or condition, i.e., arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

As used herein, the term "inhibiting" of disease or condition (e.g., fibrosis of a renal allograft and/or allograft loss) means for example, to stop the development of one or more symptoms of a disease in a subject before they occur or are detectable, e.g., by the patient or the patient's doctor. Preferably, the disease or condition does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., an immunosuppressive therapy or other anti-rejection therapy. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. Pharmaceutically acceptable derivatives include salts, solvates, esters, carbamates, and/or phosphate esters.

As used herein the terms "therapeutically effective" and "effective amount", used interchangeably, applied to a dose or amount refer to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein, e.g., fibrosis of an allograft and/or allograft loss. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using decreased fibrosis and/or decreased allograft rejection as a readout.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methyl-phosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

The terms "MicroRNA," "miR" and "miRNA" are used interchangeably and as used herein has the same meaning as typically in the art, i.e., to a processed or unprocessed RNA transcript that is capable of regulating the activity of a target mRNA. The unprocessed miR gene transcript is also called a "miR precursor," and typically comprises an RNA transcript of about 70-100 nucleotides in length. The miR precursor can be processed by digestion with an RNAseq into an active 19-25 nucleotide RNA molecule. This active 18-25 nucleotide RNA molecule is also called the "processed" miR gene transcript or "mature" miRNA.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

As used herein, the phrase "under hybridization conditions" means under conditions that facilitate specific hybridization of a subset of capture oligonucleotides to complementary sequences present in the cDNA or cRNA. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

Diagnostic Methods

The present invention relates to methods useful for the characterization of (e.g., clinical evaluation, diagnosis, classification, prediction, profiling) of an allograft recipient's risk for developing fibrosis of the allograft and/or allograft loss based on the levels or occurrence of certain analytes (e.g., miRNA).

In one embodiment, there is provided a diagnostic method of assessing n allograft recipient has higher than normal risk for developing fibrosis of the allograft and/or allograft, comprising the steps of comparing the level of expression of a 4 miRNA markers in sample and the normal level of expression of the marker in a control, e.g., a sample from a healthy individual.

A altered level, including, for example a significantly altered level of expression of the 4 miRNA markers in the recipient's sample as compared to the control (e.g., normal) level is an indication that the patient is at risk of developing fibrosis of the allograft and/or allograft loss.

As used herein, levels refer to the amount or concentration of an analyte in a sample (e.g., a plasma or serum sample) or subject. Whereas, occurrence refers to the presence or absence of a detectable analyte in a sample. Thus, level is a continuous indicator of amount, whereas occurrence is a binary indicator of an analyte. In some cases, an occurrence may be determined using a threshold level above which a biomarker is present and below which a biomarker is absent.

The miRNA markers described herein are particularly useful for characterizing (e.g., assessing or evaluating) an allograft recipient's risk for developing fibrosis of the allograft and/or allograft loss. Moreover, the methods described herein are useful for diagnosing an allograft recipient's risk for developing fibrosis of the allograft and/or allograft loss. As used herein, diagnosing includes both diagnosing and aiding in diagnosing. Thus, other diagnostic criteria may be evaluated in conjunction with the results of the methods in order to make a diagnosis.

According to some embodiments, the method comprises determining the expression level (i.e., determining the level, measuring the amount, or measuring the level) of each (i.e., all) miRNA within a panel of miRNA molecules (e.g., hsa-mir-128, hsa-mir-29b-3p, hsa-mir-302b-3p, and hsa-mir-192-5p).

The levels of the analytes for a subject can be obtained by any art recognized method. Typically, the level is determined by measuring the level of the metabolite in a body fluid (clinical sample), e.g., blood, serum, or plasma. The level can be determined by any method known in the art, e.g., polymerase chain reaction (PCR), quantitative (q)PCR, or microarray, or other known techniques for determining the presence and/or quantity of miRNA.

In some cases, the methods disclosed herein involve comparing expression levels or occurrences to a reference. The reference can take on a variety of forms. In some cases, the reference comprises predetermined values for the plurality of miRNA (e.g., each of the plurality of miRNA). The predetermined value can take a variety of forms. It can be a level or occurrence of an analyte obtained from an allograft recipient previously diagnosed as being at risk for fibrosis of the allograft and allograft loss, or obtained from a an allograft recipient known not to be at risk for fibrosis of the allograft and allograft loss (e.g., an asymptomatic subject). It can be a level or occurrence obtained from a subject having not received a renal allograft. It can be a level or occurrence in the same recipient, e.g., at a different time point. A predetermined value that represents a level(s) of an analyte is referred to herein as a predetermined level. A predetermined level can be single cut-off value, such as a median or mean. It can be a range of cut-off (or threshold) values, such as a confidence interval. It can be established based upon comparative groups, such as where the risk in one defined group is a fold higher, or lower, (e.g., approximately 2-fold, 4-fold, 8-fold, 16-fold or more) than the risk in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk. Moreover, the reference could be a calculated reference, most preferably the average or median, for the relative or absolute amount of an analyte of a population of individuals comprising the subject to be investigated. The absolute or relative amounts of the analytes of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 subjects. It is to be understood that the subject to be diagnosed by the method of the present invention and the subjects of the said plurality of subjects are of the same species.

Subjects associated with predetermined values are typically referred to as control subjects (or controls). A control subject may or may not have received a renal allograft. In some cases it may be desirable that control subject is a symptomatic subject, and in other cases it may be desirable that a control subject is an asymptomatic subject.

In some methods herein, it is desirable to detect and quantify RNAs, including miRNAs, present in a sample. Detection and quantification of RNA expression can be achieved by any one of a number of methods well known in the art. Using the known sequences for miRNA family members, specific probes and primers can be designed for use in the detection methods described below as appropriate.

In some cases, detection and quantification of RNA expression requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs). Extraction procedures such as those using QIAGEN-ALLprep kit are also contemplated.

A level, in some embodiments, may itself be a relative level that reflects a comparison of levels between two states. Relative levels that reflect a comparison (e.g., ratio, difference, logarithmic difference, percentage change, etc.) between two states (e.g., healthy and diseased) may be referred to as delta values. The use of relative levels is beneficial in some cases because, to an extent, they exclude measurement related variations (e.g., laboratory personnel, laboratories, measurements devices, reagent lots/preparations, assay kits, etc.). However, the invention is not so limited.

Expression levels and/or reference expression levels may be stored in a suitable data storage medium (e.g., a database) and are, thus, also available for future diagnoses. This also allows efficiently diagnosing prevalence for a disease because suitable reference results can be identified in the database once it has been confirmed (in the future) that the subject from which the corresponding reference sample was obtained did develop fibrosis of the allograft and/or experience allograft rejection. As used herein a "database" comprises data collected (e.g., analyte and/or reference level information and/or patient information) on a suitable storage medium. Moreover, the database, may further comprise a database management system. The database management system is, preferably, a network-based, hierarchical or object-oriented database management system. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative of renal allograft rejection risk. Thus, if an identical or similar data set can be identified in the data collection, the test data set will be associated with renal allograft rejection risk. Consequently, the information obtained from the data collection can be used to diagnose an allograft recipient's risk for developing fibrosis of the allograft and/or allograft loss or based on a test data set obtained from a subject. More preferably, the data collection comprises characteristic values of all analytes comprised by any one of the groups recited above.

Also provided are databases of gene expression/protein signatures of different transplant categories, e.g., AR, STA, NS and the like. The gene expression/protein signatures and databases thereof may be provided in a variety of media to facilitate their use (e.g., in a user-accessible/readable format). "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

In one aspect, the methods disclosed herein comprise diagnosing the recipient's risk include calculating the recipient's risk by applying the expression levels determined in the recipient's sample to a penalized logistic regression fitting model. In some embodiments, the penalized logistic regression fitting model from which the risk will be calculated utilizes the formula:

$$\log\frac{p(x)}{1-p(x)} = \beta^*_{0+}\beta^*_1 g_1 + \beta^*_i g_i + \ldots + \beta^*_4 g_4$$

where (p(x) is the probability of developing fibrosis, $\beta^*_i$ is penalized coefficiency and $g_i$ is the expression value of miRNA i. The penalized logistic regression fitting model can be used to compute a probability score that represents the risk for developing fibrosis of the allograft and allograft loss. The probability score can be determined using a computer based system. In some aspects, probability score is used to determine the cut off value.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan with a ranking of similarities and identifies the degree of similarity contained in the test expression profile.

In a typical embodiment, a clinical lab will obtain the expression value using the patient's sample and send it to the patient's doctor. The doctor will then communicate this value to his web based service provider. The service provider will enter that value in the bioinformatics system which already has the penalized coefficiency for each gene of the preselected gene set and the cutoff from the logistic regression model from the training set. The bioinformatics system will use this information to calculate the probability score for the patient. The calculated score will reflect the patient's risk status.

The invention further provides for the communication of assay results or diagnoses or both to technicians, physicians or patients, for example. In certain embodiments, computers will be used to communicate assay results or diagnoses or both to interested parties, e.g., physicians and their patients.

In some embodiments, the method disclosed herein further comprise modifying the recipient's clinical record to identify the recipient as being at risk for developing fibrosis of the allograft and/or allograft loss. The clinical record may be stored in any suitable data storage medium (e.g., a computer readable medium).

In some embodiments of the invention, a diagnosis based on the methods provided herein is communicated to the allograft recipient as soon as possible after the diagnosis is obtained. The diagnosis may be communicated to the recipient by the recipient's treating physician. Alternatively, the diagnosis may be sent to a recipient by email or communicated to the subject by phone. The diagnosis may be sent to a recipient by in the form of a report. A computer may be used to communicate the diagnosis by email or phone. In certain embodiments, the message containing results of a diagnostic test may be generated and delivered automatically to the recipient using a combination of computer hardware and software which will be familiar to artisans skilled in telecommunications.

Aspects of the present invention include computer program products for identifying a subject who has undergone a renal allograft and is at risk for developing fibrosis of the allograft and allograft loss, wherein the computer program product, when loaded onto a computer, is configured to employ a miRNA expression result from a sample derived from the subject to determining whether a subject who has undergone a renal allograft is at risk risk for developing fibrosis of the allograft and allograft loss wherein the gene expression result comprises expression data at least for the 4 miRNA panel provided herein.

Also provided are reference expression profiles for a phenotype that is one of: (a) low risk for developing fibrosis of the allograft and allograft loss; or (b) high risk risk for developing fibrosis of the allograft and allograft loss; wherein the expression profile is recorded on a computer readable medium that is accessible by a user, e.g., in a user readable format. In certain embodiments, the expression profile includes. In certain embodiments, the expression profile is a profile for a phenotype that is low risk. In certain embodiments, the expression profile is a profile for a phenotype that is high risk.

The invention also may provide kits for evaluating miRNA expression levels in a subject (e.g. a renal allograft recipient). The kits of the invention can take on a variety of forms. Typically, the kits will include reagents suitable for determining miRNA expression levels (e.g., those disclosed herein) in a sample. Optionally, the kits may contain one or more control samples. Also, the kits, in some cases, will include written information (indicia) providing a reference (e.g., predetermined values), wherein a comparison between the miRNA expression levels in the subject and the reference (predetermined values) is indicative of a clinical status.

In some cases, the kits comprise software useful for comparing miRNA expression levels or occurrences with a reference (e.g., a prediction model). Usually the software will be provided in a computer readable format such as a compact disc, but it also may be available for downloading via the internet. However, the kits are not so limited and other variations with will be apparent to one of ordinary skill in the art. The present methods can also be used for selecting a treatment and/or determining a treatment plan for a subject, based on the occurrence or levels of miRNA (e.g., those disclosed herein). In some embodiments, using the methods disclosed herein, a health care provider (e.g., a physician) identifies a recipient as being at risk for developing fibrosis of the allograft and/or allograft loss, and, based on this identification the health care provider determines an adequate management plan for the subject. In some embodiments, using the method disclosed herein, a health care provider (e.g., a physician) diagnoses a recipient as being at risk for developing fibrosis of the allograft and/or allograft loss based on the occurrence or levels of certain miRNA in a clinical sample obtained from the subject, and/or based on a classification of a clinical sample obtained from the subject. By way of this diagnosis the health care provider determines an adequate treatment or treatment plan for the subject as described herein. In some embodiments, the methods further include administering the treatment to the subject.

An exemplary procedure describing the application of a 4 miRNA panel as described herein for the diagnosing a renal allograft recipient's risk for developing fibrosis of the allograft and allograft loss is provided as follows:

1) Selecting training group: A group of kidney transplant patients with high and low risk of cases (total number N=~100) will be carefully selected. The training group should have well-characterized demographics and clinical indications which have been reviewed by at least two pathologists.

2) Measuring Expression of 4 miRNAs:

Expression levels of 4 miRNAs from the blood sample post-transplant of each patient in the training group will be measured by Microarray, RT-PCR or Nanostring technology. Use of these techniques is described in the examples below.

3) Establishing Regression Model and Cut Off:

A penalized logistic regression fitting model using logistf R package will be then applied on expression values of 4 miRNAs to derive the statistical model from which the β* value will be derived for each miRNA and the probability score of acute rejection for each patient will be calculated.

$$\log \frac{p(x)}{1-p(x)} = \beta_{0+}^* \beta_1^* g_1 + \beta_i^* g_i + \ldots + \beta_4^* g_4$$

where (p(x) is the probability of developing fibrosis, $\beta^*_i$ is penalized coefficiency and $g_i$ is the expression value of miRNA i.

Based on the probability score, the prediction statistics such as prediction AUC (area under the curve) of ROC (Receive operating characteristic) curve of true positive rate versus false positive, sensitivity/specificity, the positive values (PPV) and negative predictive values (NPV) will be determined. At a given specificity (90%), a probability score cut off will be established which best predicts the development of fibrosis. This may be a clear cut off into two groups in that if they are in the top group they have a high likelihood of developing fibrosis and the test is determined to be positive but if they are in the bottom they have a very low likelihood of developing fibrosis and the test is determined to be negative. The alternative is that patients may be broken in to tertiles based on their probability score determined as above. In this case if the patient is in (1) the top tertile they have a high likelihood of developing fibrosis and the test is determined to be positive; (2) they are in the second tertile or intermediate group their risk cannot be accurately determined; and (3) they are in the bottom they have a very low likelihood of developing fibrosis and the test is determined to be negative.

The coefficiency ($\beta^*$ value) and the cutoff derived from the training group will be entered and stored into a web-based bioinformatic system which can be accessed from clinical lab/doctor office via the internet.

4) Diagnostic criteria:

For a new patient, the expression levels of 4 miRNA set will be measured by the same technology as used for the training set in the clinical lab. By using a web-based bioinformatics system, the probability score will be calculated by summarizing expression value ($g_i$) of miRNA multiplied by their pi values which are derived from the training set and the probability score will be compared to the cutoff to determine the likelihood of development of fibrosis. The clinical result will send the testing results to the doctor where if the result for the sample is above our cutoff for high likelihood of fibrosis the test will be reported as positive, and if it is below our cutoff for low likelihood of fibrosis it will be reported as negative.

5) Treatment:

If the tests indicates that the patient has high risk of developing fibrosis of the allograft and allograft loss can be treated, for example, and without limitation, by the administering to the allograft recipient an anti-fibrosis drug to the allograft recipient or switch immunosuppression.

Methods of Treating

In some embodiments of the disclosure, the methods disclosed herein include treating the allograft recipient to inhibit fibrosis of the allograft and allograft loss (rejection) if the allograft recipient has been diagnosed as being at risk (e.g., at high risk) for fibrosis of the allograft and allograft loss. The methods for determining whether a patient is at high risk, and should be treated with an intervention are described above.

In some embodiments, the treatment includes modification of the allograft recipient's immunosuppression regimen, such as, for example, by administering, discontinuing administration, or adjusting the dosage of one or more immunosuppressive drugs, including, for example, or one or more anti-rejection drugs.

In some embodiments, the treatment includes administering the allograft recipient an anti-rejection drug to the allograft recipient.

Allograft recipients identified as being at high risk for developing fibrosis of the allograft and allograft loss can be treated, for example, and without limitation, by the administration of immunosuppressive drugs. Immunosuppression can be achieved with many different drugs, including steroids, targeted antibodies and CNIs, like tacrolimus. Non-limiting examples include, e.g. a calcineurin inhibitor (CNI), such as cyclosporine or tacrolimus, or a less fibrogenic immunosuppressive drug such as mycophenolate mofetil (MMF) or sirolimus. The main class of immunosuppressants is the calcineurin inhibitors (CNIs), which includes tacrolimus (Prograf® and Advagraf®/Astagraf XL (Astellas Pharma Inc.) and generics of Prograf®) and cyclosporine (Neoral® and Sandimmune® (Novartis AG) and generics). Steroids such as prednisone may also be administered to treat patients at risk for developing fibrosis of the allograft and allograft loss. Antiproliferative agents such as Mycophenolate Mofetil, Mycophenolate Sodium and Azathioprine are also useful in such treatments. Of these, tacrolimus is one of the more potent in terms of suppressing the immune system. The anti-rejection drug Belatacept (Bristol Myers Squibb) may also be employed for treatment of patients at risk for rejection or fibrosis.

Allograft recipients identified as being at high risk for developing fibrosis of the allograft and allograft loss can be treated, for example, and without limitation, by the treatment of the allograft recipient with an anti-fibrosis drug or by modifying the allograft recipients immunosuppression regimen. Thus, treatment of the allograft recipient may include administering, discontinuing administration, or adjusting the dosage of one or more anti-fibrosis drugs. In some aspects, the anti-fibrosis drug may include an anti-fibrotic agents such as, for example, Pirfenidone, relaxin, Bone morphogenetic protein 7 (BMP-7), and Hepatic growth factor (HGF) 6.

Administration of an angiotensin converting enzyme inhibitor (ACEI) such as lisinopril, or angiotensin II receptor blockades such as losartan, to such patients is also within the scope of the present disclosure.

In some aspects, the method includes switching immunosuppression from a calcineurin inhibitor to a drug which is not associated with the development of fibrosis such as the anti-rejection drug is Belatacept, rapamycin or Mycophenolate Mofetil.

Administration of an angiotensin converting enzyme inhibitor (ACEI) such as lisinopril, or angiotensin II receptor blockades such as losartan, to such patients is also within the scope of the present disclosure.

Kits

In certain embodiments, kits are provided for determining a renal allograft recipient's risk of developing fibrosis of the allograft and allograft loss. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The above kits can include barcode probes that specifically hybridize to one or more of hsa-mir-128, hsa-mir-29b-3p, hsa-mir-302b-3p, and hsa-mir-192-5p (e.g., for use in Nanostring analysis). The kits can further contain one or more miRNA extraction reagents and/or annealing reagents.

In some embodiments, the kits will contain the primers for amplifying a miRNA selected from the group consisting of hsa-mir-128, hsa-mir-29b-3p, hsa-mir-302b-3p, and hsa-mir-192-5p; and optionally comprising primers for amplifying control sequences, such as, for example, primers for amplifying beta actin (ACTB) and glyceraldehyde 3-phosphate dehydrogenase (GAPDH), 18S ribosomal RNA (for qPCR assays), and fragments thereof.

In other embodiment, a kit can contain an miRNA inhibitor (e.g., targeted to an miRNA that is upregulated in allograft recipients at high risk of developing fibrosis of the allograft and allograft loss (e.g., hsa-miR-128, hsa-miR- 182-5p, hsa-miR-151a-5p, hsa-miR-30c-5p, hsa-miR-302b-3p, hsa-miR-378e, hsa-miR-30b-5p, hsa-miR-23b-3p, hsa-miR-423-5p, hsa-miR-26a-5p, hsa-miR-423-5p, hsa-miR-26a-5p, hsa-miR-186-5p, hsa-miR-361-5p, and hsa-miR-22-3p)).

The kits, regardless of type, will generally comprise one or more containers into which the biological agents are placed and, preferably, suitably aliquotted. The components of the kits may be packaged either in aqueous media or in lyophilized form. The kits can also comprise one or more pharmaceutically acceptable excipients, diluents, and/or carriers. Non-limiting examples of pharmaceutically acceptable excipients, diluents, and/or carriers include RNAse-free water, distilled water, buffered water, physiological saline, PBS, Ringer's solution, dextrose solution, reaction buffers, labeling buffers, washing buffers, and hybridization buffers.

The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits contemplated herein can further contain one or more mRNA extraction reagents and/or reagents for cDNA synthesis.

The kits for using miRNA arrays for therapeutic, prognostic, or diagnostic applications and such uses are contemplated. The kits can include a miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

Nanostring Assay

Nanostring Assay Kit Will Include:

1) Custom CodeSet (barcoded probesets for 4 miRNA panel including 3 house-keeping miRNA and negative controls provided by Nanostring)

2) nCounter® Master Kit including nCounter Cartridge, nCounter Plate Pack and nCounter Prep Pack 3) All prep kit (QIAGEN-ALLprep kit, Valencia, Calif. USA)

Nanostring Experiments:

The total RNA will be extracted using All prep kit (QIAGEN-ALLprep kit, Valencia, Calif. USA) by following the manufactures protocol; Barcode probes will be annealed to the total RNA in solution at 65° C. with the master kit. The capture probe will capture the target to be immobilized for data. After hybridization, the sample will be transferred to nCounter Pre Station and probe/target will be immobilized on the nCouter Cartridge and the probes were then counted by nCounter Digital Analyzer.

miRNA Transcriptomic Data Analysis

The raw count data from Nanostring analyzer will be processed in the following procedure: the raw count data will be firstly normalized to the count of the house-keeping miRNA and the miRNAs with counts lower than the median plus 3 standard deviation of the counts of negative controls will be filtered out. Due to data variation arising from reagent lot, the count for each mRNA from different reagent lots will be calibrated by multiplying a factor of the ratio of the averaged counts of the samples on different reagent lots. The calibrated counts from different experimental batches will be further adjusted by ComBat package.

qPCR Assay or qPCR Array Assay qPCR Assay Kit Includes:

1) Primer container (8 tubes with one qPCR assay per tube for 4 miRNA panel and 3 reference miRNAs and the control probe 5s RNA). The assays will be ordered from LifeTech, or qPCR arrays deposited with qPCR assays in the wells of a 96-well plate 2) NCode™ VILO™ cDNA 3) TaqMan® ARRAY 96-WELL PLATE 6×16

4) NCode™ EXPRESS SYBR® GreenER™ miRNA qRT-PCR Kits

Experimental Procedure and Data Analysis:

Total RNA will be extracted from allograft biopsy samples using All prep kit (QIAGEN-ALLprep kit, Valencia, Calif. USA). cDNA will be synthesized using NCode™ VILO™ miRNA cDNA Synthesis (LifeTech). TaqMan qPCR assays for the 4 miRNAs, 3 reference miRNA and 5s rRNA will be purchased from ABI Life Technology (Grand Island, N.Y.). qPCR experiments will be performed on cDNA using NCode™ EXPRESS SYBR® miRNA qRT-PCR Kits (LifeTech) and PCR reactions will be monitored and acquired using an ABI7900HT system. Samples will be measured in triplicates. Cycle Times (CT) values for the prediction miRNA set as well as the 3 references will be generated. The ΔCT value of each miRNA will be computed by subtracting the average CT value for the reference miRNA from the CT value of each miRNA.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

Example 1

Methods and Materials
Total RNA Extraction:

Total RNA was extracted from blood samples obtained at 3 month after transplantation using All prep kit (QIAGEN-ALLprep kit, Valencia, Calif. USA). RNA quality was assessed using Bioanalyzer 2100 (Agilent Technologies).

RNA Sequencing:

Total RNA from blood samples of 96 recipients 3 months after transplantation was extracted using Trizol, and the RNA quality was assessed by the Bioanalyzer 2100 (Agilent Technologies). The libraries were generated by following the manufacturer's protocol and were sequenced on Illumina HisSeq2000 sequencer. Briefly, mRNA was extracted from 2 μg of total RNA using oligo-dT magnetic beads and fragmented at high temperature. A cDNA library was then prepared from the fragmented mRNA by reverse transcription, second strand synthesis and ligation of specific adapters. Next generation sequencing was performed on Illumina Hiseq 2000 with single-ended 51 read cycles. Image analysis and bases calling was conducted in real-time by the Illumina analysis pipeline.

The raw RNAseq data was processed according to the following procedure: Reads with good quality were first aligned to several human reference databases including hg19 human genome, exon, splicing junction and contamination database including ribosome and mitochondria RNA sequences using BWA alignment algorithm. After filtering reads mapped to contamination database, the reads that are uniquely aligned to the exon and splicing-junction sites with a maximal 2 mismatches for each transcript were then counted as expression level for corresponding transcript and further subjected to quantile normalization cross samples after log 2 transformation.

Nanostring Experiments:

miRNA profiling of blood samples of 102 transplant patients was performed with Nanostring by following the manufactures protocol. Briefly, the NanoString nCounter human microRNA V2 expression assay on 800 human miRNAs (NanoString Technologies) was used to anneal 100 ng input miRNAs to target specific barcode probes. The sample was immobilized on an nCounter Cartridge using the nCounter Prep Station and the probes were then counted by nCounter Digital Analyzer.

MicroRNA Transcriptomic Data Analysis

The raw count data from Nanostring analyzer was processed in the following procedure (see FIG. 1). The raw count data were normalized to the top 100 expressed microRNAs (miRNAs), and the miRNAs with counts lower than the median plus 3 standard deviations of the counts of negative controls were filtered out. Due to data variation arising from reagent lot, the count for each miRNA from different reagent lots was calibrated by multiplying a factor of the ratio of the averaged counts of the samples on different reagent lots. The calibrated counts from different experimental batches were further adjusted by ComBat package.

To identify differentially expressed miRNA in patients with high CADI ($>1$) compared to low CADI ($<=1$) (as defined by Yilmaz et al., 2003, Journal of the American Society of Nephrology: JASN. 14:773-779), the surrogated variable analysis (SVA) bioconductor package was applied on batch adjusted data to identify and remove unknown variations against these two groups. LIMMA (Linear Models for Microarray Data) test were then performed to identify differentially expressed miRNA with a cutoff pvalue<0.05.

To investigate the biological processes the differentially expressed miRNA might be involved in, the gene expression data from RNAseq and miRNA data on the same patients were correlated. The Pearson correlation coeffficiency between expression values of miRNA and its predicted gene targets (http://www.microRNA.org) and negatively correlated genes were selected at p<0.05 and subjected to network analysis and Gene Ontology enrichment analysis.

miRNA Prediction Set Identification

To identify an optimal miRNA set to predict the progression of kidney fibrosis, the 102 patients were divided into training set (N=68) and testing set (N=34). The training set was subjected to SVA adjustment to remove unwanted variables for high (CADI>1) and low (CADI<=1) CADI groups. Characteristic demographics the 102 patients (training set (N=68) and testing set (N=34)) are provided in Table 1.

TABLE 1

| Characteristics | Cohort n = 102 Mean ± SD (%) | Training High CADI-12 Mean ± SD (%) (n = 36) | Training Low CADI-12 Mean ± SD (%) (n = 32) | P-value1 | Test High CADI-12 Mean ± SD (%) (n = 18) | Test Low CADI-12 Mean ± SD (%) (n = 16) | P-value2 |
|---|---|---|---|---|---|---|---|
| Recipient age | 48.96 ± 12.9 | 51.4 ± 13.1 | 46.5 ± 11.8 | 0.08 | 47.3 ± 14.0 | 50.1 ± 13.6 | 0.59 |
| Recipient gender - Female | 38 (37.2) | 14 (38.8) | 8 (33.3) | 0.30 | 10 (55.5) | 6 (37.5) | 0.32 |
| Recipient race | | | | 0.26 | | | 0.10 |
| White | 69 (67.6) | 21 (58.3) | 24 (75.0) | | 12 (66.7) | 12 (75.0) | |
| African-American | 15 (14.7) | 5 (13.9) | 4 (12.5) | | 2 (11.1) | 4 (25.0) | |
| Other/Unreported | 18 (17.7) | 10 (27.7) | 4 (12.5) | | 4 (22.2) | 0 (0) | |
| Donor age | 40.2 ± 15.7 | 47.2 ± 8.2 | 33.6 ± 13.1 | <0.01 | 41.1 ± 15.8 | 41.3 ± 15.2 | 1.0 |
| Donor gender - Female | 49 (43.7) | 19 (52.7) | 15 (46.8) | 0.23 | 8 (44.4) | 7 (43.7) | 0.59 |
| Donor race | | | | 0.98 | | | 0.69 |
| Caucasian | 83 (81.4) | 29 (80.6) | 26 (81.3) | | 15 (83.3) | 13 (81.3) | |
| African-American | 7 (6.9) | 2 (5.5) | 2 (6.2) | | 1 (5.55) | 2 (12.5) | |
| Other/Unreported | 12 (11.7) | 5 (13.9) | 4 (12.5) | | 2 (11.2) | 1 (6.2) | |
| Donor status-Deceased/Living | 57/45 | 19/17 | 19/13 | 0.29 | 11/7 | 8/8 | 0.73 |
| Induction therapy Y/N | 79/23 | 30/6 | 23/9 | 0.38 | 14/4 | 12/4 | 1.0 |

TABLE 1-continued

| Characteristics | Cohort n = 102 Mean ± SD (%) | Training High CADI-12 Mean ± SD (%) (n = 36) | Training Low CADI-12 Mean ± SD (%) (n = 32) | P-value1 | Test High CADI-12 Mean ± SD (%) (n = 18) | Test Low CADI-12 Mean ± SD (%) (n = 16) | P-value2 |
|---|---|---|---|---|---|---|---|
| Lymphocyte depleting | 36 (45.6) | 12 (40.0) | 11 (47.8) | 0.58 | 7 (50.0) | 6 (50.0) | 1.0 |
| Anti-CD25 therapy | 43 (54.4) | 18 (60.0) | 12 (52.2) | | 7 (50.0) | 6 (50.0) | |
| CADI-score 3 months | 1.49 ± 1.8 | 2.18 ± 2.2 | 0.82 ± 1.2 | <0.01 | 1.92 ± 2.2 | 1.12 ± 1.2 | 0.33 |
| CADI-score 12 months | 2.69 ± 2.6 | 4.52 ± 2.4 | 0.28 ± 0.4 | <0.0001 | 4.05 ± 1.5 | 0.68 ± 0.5 | <0.0001 |
| Probability Score** | 0.52 ± 0.29 | 0.72 ± 0.22 | 0.31 ± 0.24 | <0.0001 | 0.75 ± 0.25 | 0.38 ± 0.24 | <0.001 |

Legend:
CADI—chronic allograft damage index at 12-months;
P-value1—comparison of Column 2 with column 3,
P-value2—comparison of column 5 with column 6 (unpaired T test or non-parametric test; ANOVA or non-parametric means)

LIMMA test was performed on SVA-adjusted training set to identify differentially expressed miRNA in patients with high CADI (compared to low CADI and the expression data of the differentially expressed miRNAs was fitted into the penalized logistic regression model for prediction of high and low CADI. The miRNAs with significant association with high/low CADI (p<0.05) were identified as optimal prediction set from the regression model. The AUC score and sensitivity and specificity were calculated from logistic regression model using the final gene set. We compared the receiver operating characteristic curves of the final optimal set to randomly selected gene sets of equal size for predicting high vs. low CADI to demonstrate that the final optimal geneset gave the best prediction. One thousand randomly selected miRNA sets were selected and AUCs of these miRNA sets were calculated and compared to the AUC of the final optimal set.

This final optimal set was cross-validated using a 3-fold cross-validation method. (FIG. 9) Briefly, the patients were randomly divided into 3 groups of equal size and equal number of high and low CADI patients and the data for any two groups were used as the training set with the third as the prediction set. The penalized logistic regression model that was built on the training set was applied on the prediction set to predict the outcome and the true and false positive rates. Prediction accuracy was calculated from the prediction data set and then averaged from three possible permutations. We repeated the steps over 100 times. The overall true or false positive rates and prediction accuracy were computed. The distribution of AUCs on the testing set based on the model derived using the training set for 100 iterations was plotted.

Finally the prediction set was validated on the testing set. The SVA model built on training set was then used to adjust each sample in the testing set and the logistic regression model built on the training set using the prediction set was applied on the adjusted training set to calculate the prediction probability for each sample. The ROC curve based on these probabilities was drawn and the AUC score for the ROC curve was computed. The logistic regression model of the training set built from a randomly selected miRNA set was also applied to the prediction set and the AUC of the training set from 100 iterations of random selection of prediction set was compared to the original AUC from the optimal set.

Figure 5:
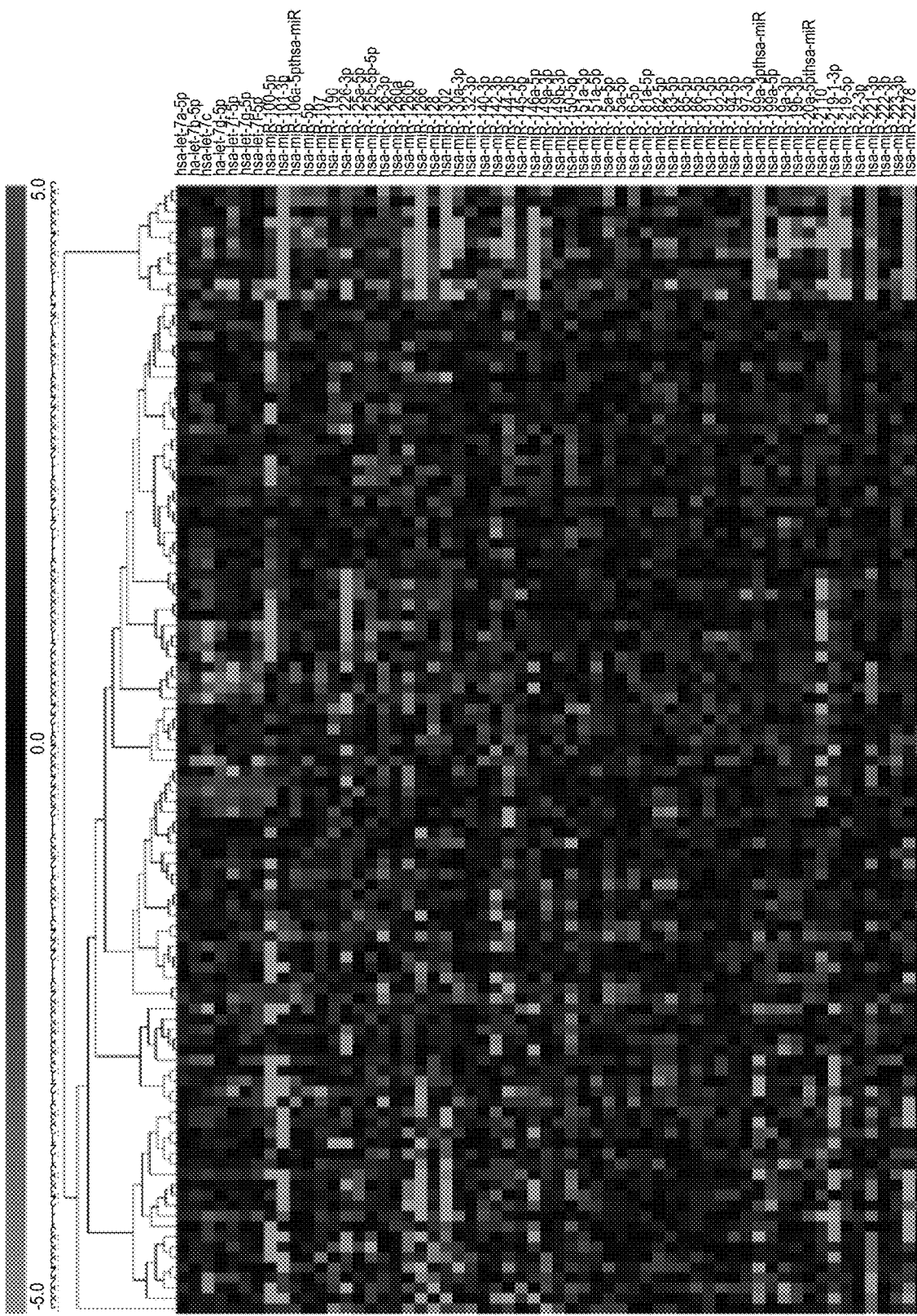
FIG. 5 is a heat map showing sample clustering after lot calibration and batch-effect removal for the indicated miRNAs.
Figure 6:
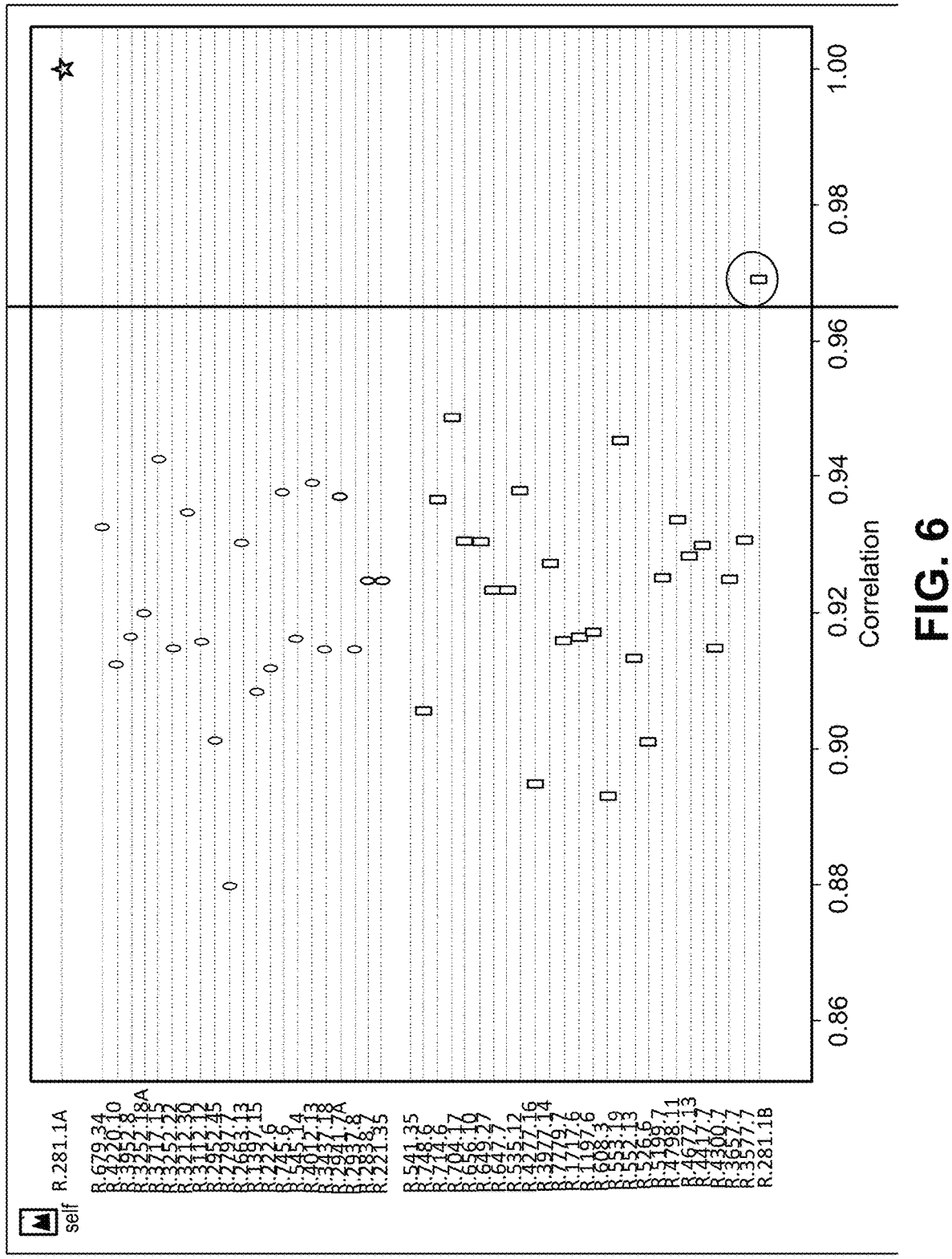
FIG. 6 shows data correction of duplicated sample R281.1 in different batches.
Figure 6:
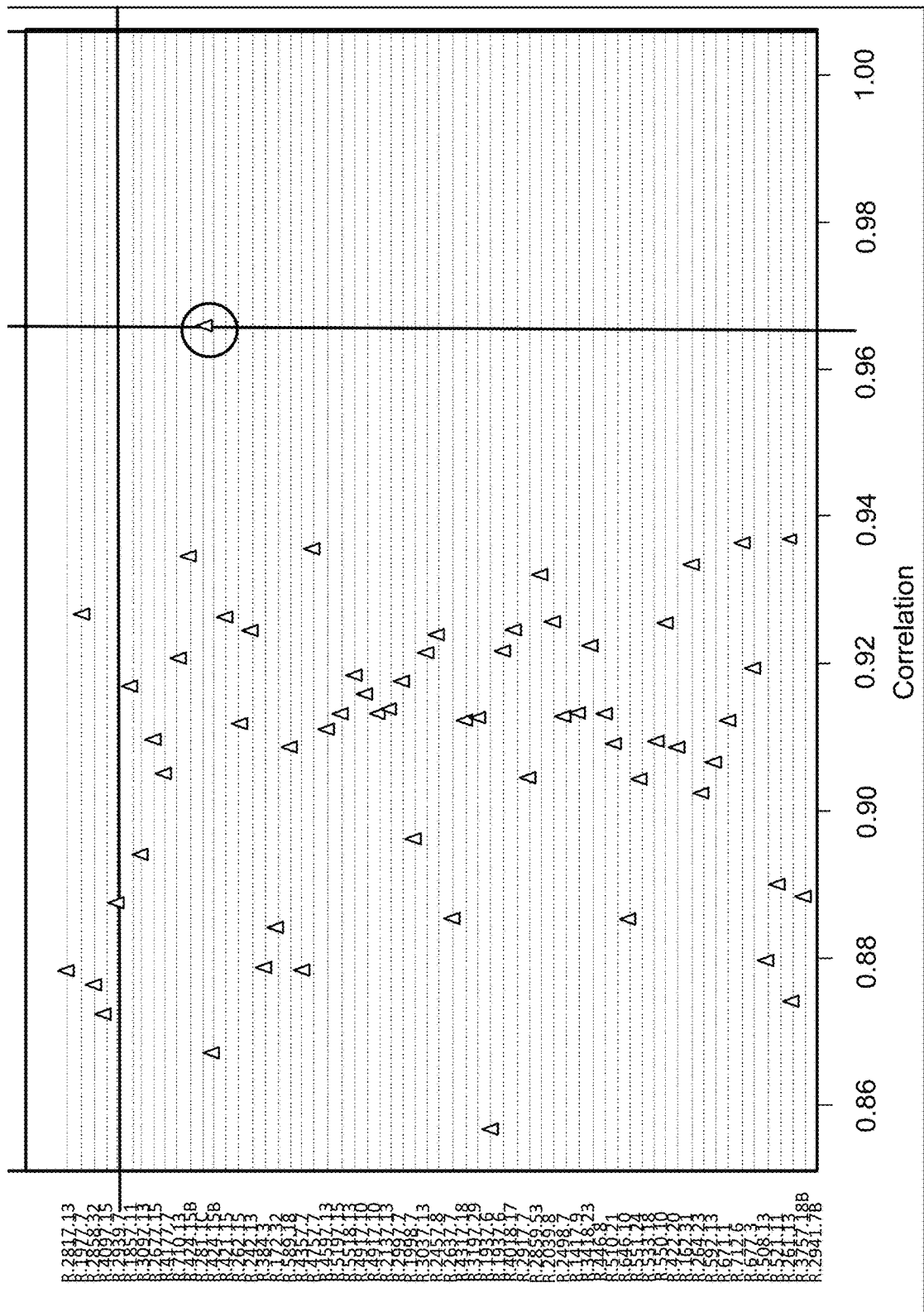
Figure 7:
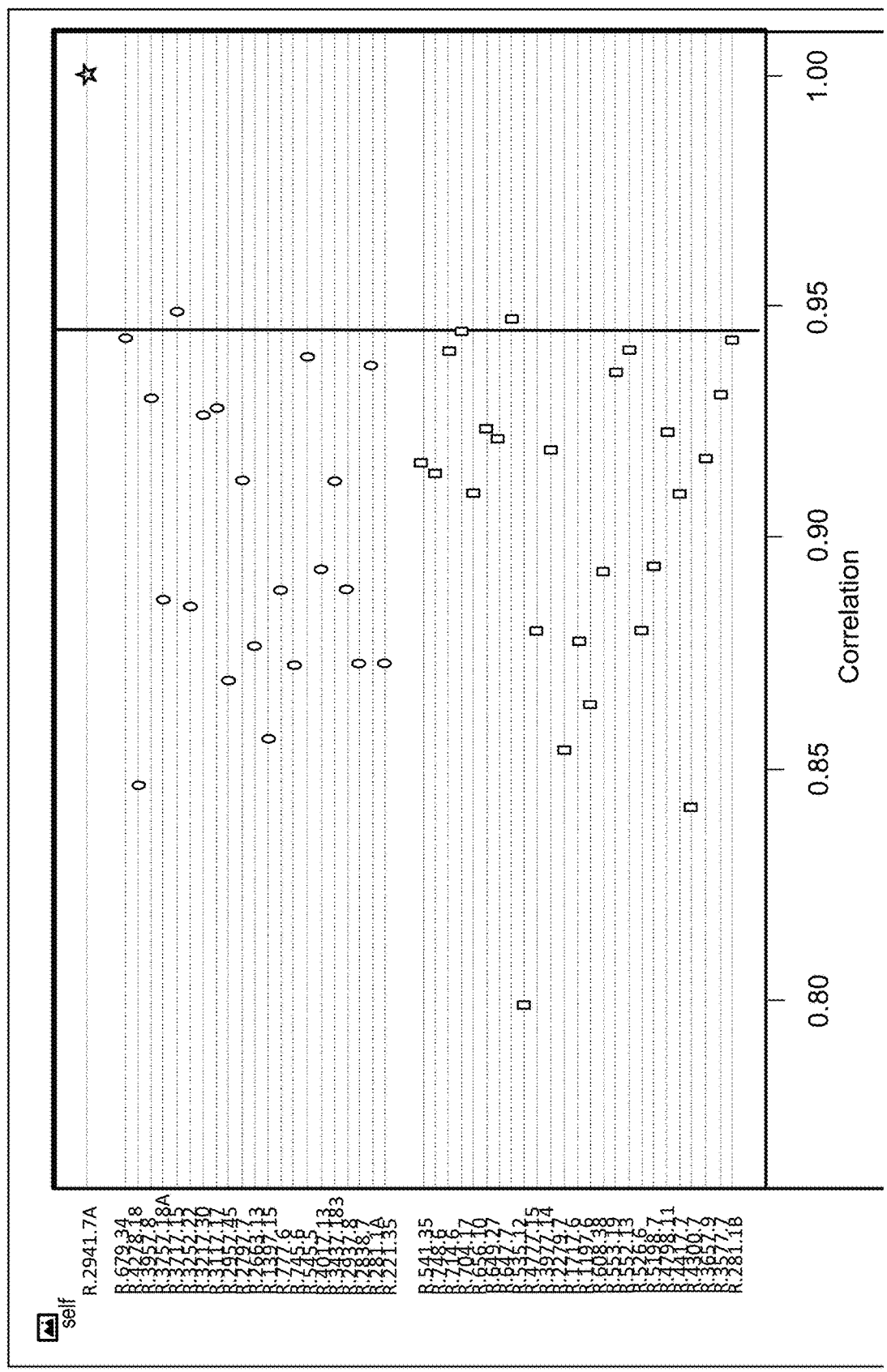
FIG. 7 shows data correction of duplicated sample R2941.7A in different batches.
Figure 7:
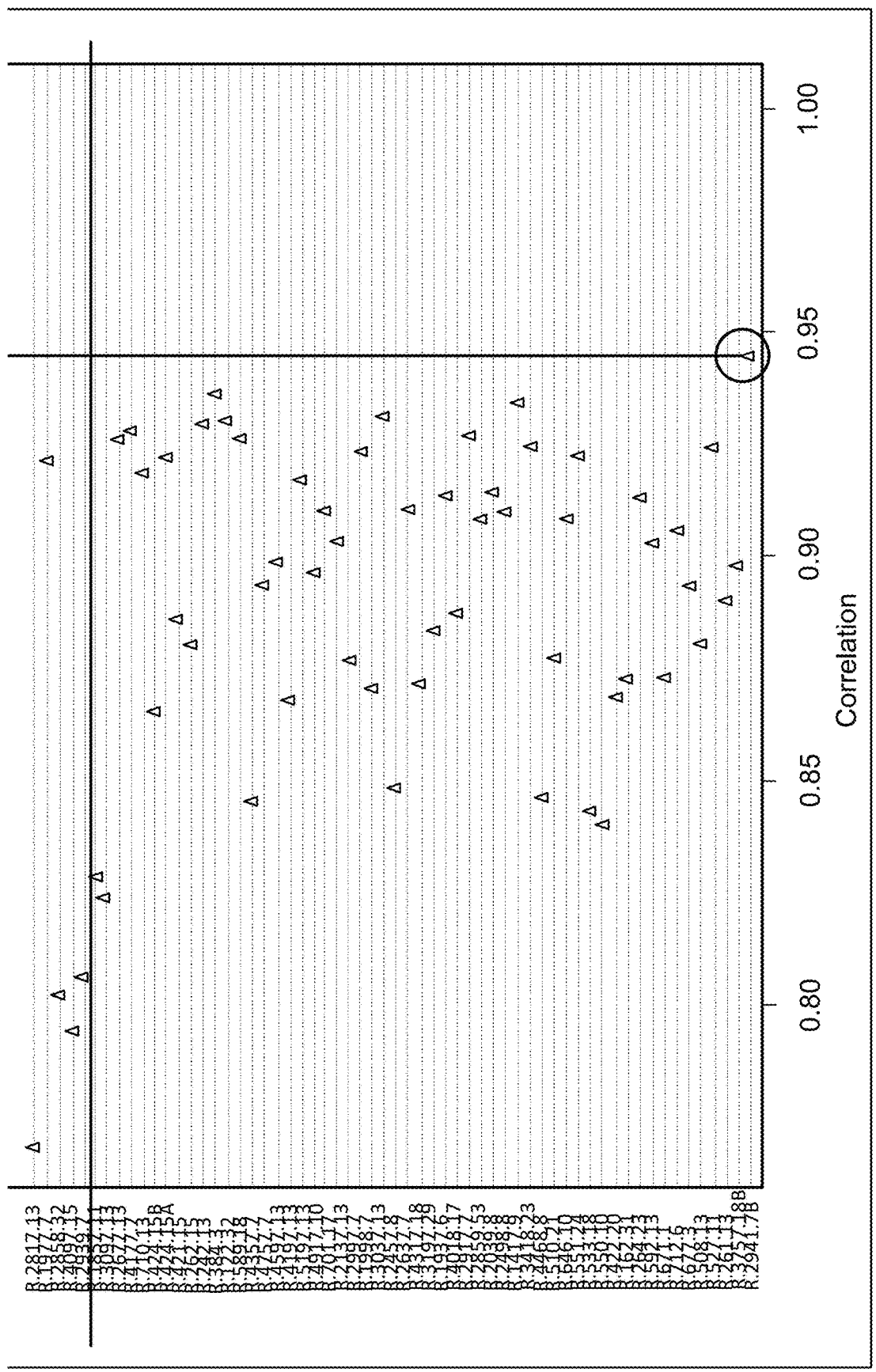

Results miRNA Transcriptomic Analysis:

To study the roles of blood miRNAs in development of kidney fibrosis, miRNA expression profiling was performed on blood samples at 3 months after transplant of 102 kidney transplant patients using Nanostring human expression assay kit for human 800 miRNA detection. The data was processed in the procedure depicted in FIG. 1 Box 1 ("Data Processing"). After normalization and stringent filtering, the final 134 miRNA passed QC with good quality and the data were then successfully adjusted for variations from reagent lots and experimental batches (FIG. 5). We observed that the data of two replicated samples from different batches/lots were very reproducible with correlation coefficiency R>0.94 (FIG. 6 and FIG. 7). All these together indicated that high quality data was generated from NanoString technology.

Figure 2:
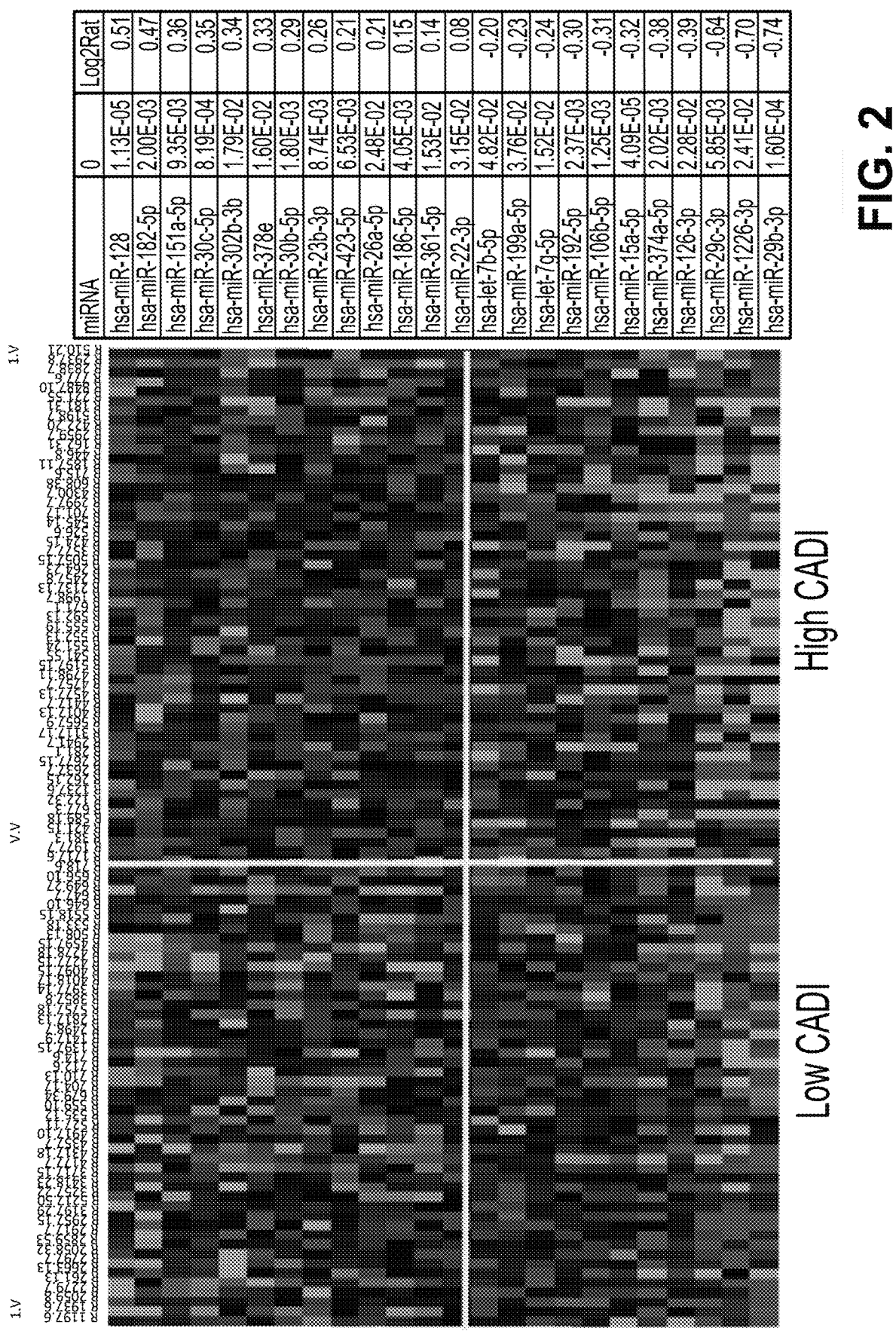
FIG. 2 contains a heat map of differentially expressed miRNAs in patients with high CADI (CADI>1) compared to low CADI (CADI<=1). Red indicates increased expression and green indicates decreased expression.
Figure 3A:
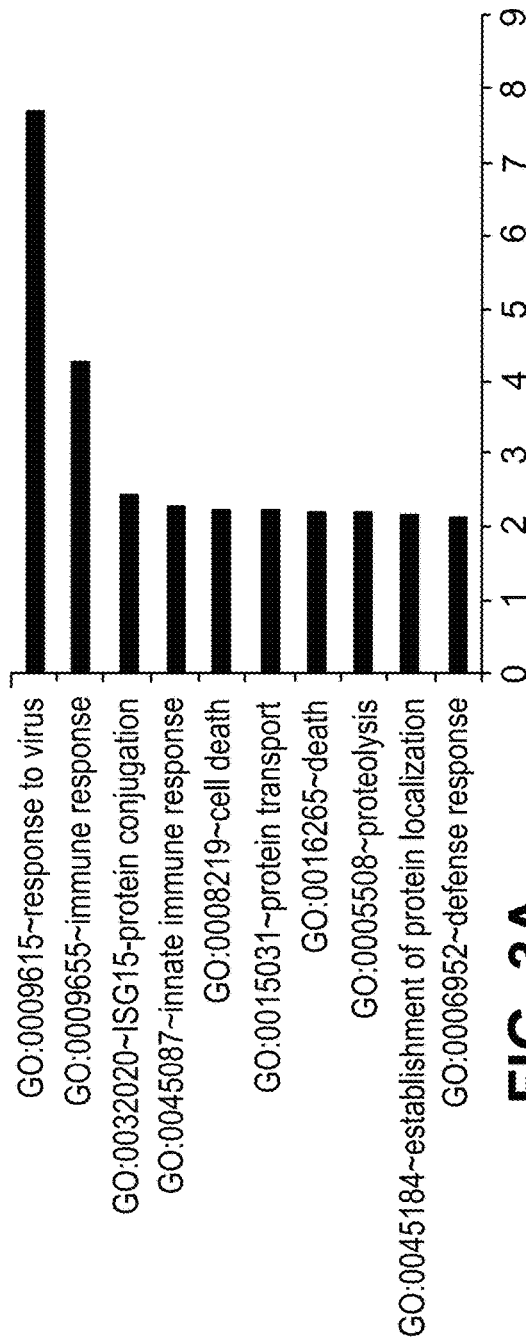
FIG. 3a contains a Gene Ontology enrichment bar chart of predicted targets that were negatively correlated with mir128.
Figure 3B:
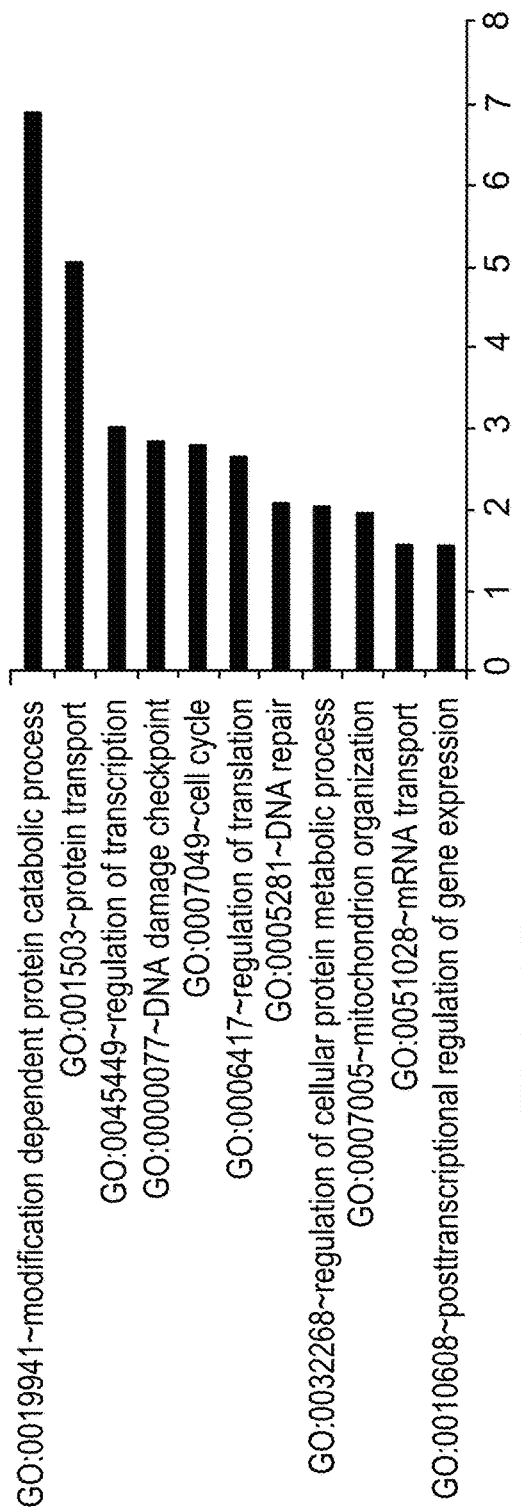
FIG. 3b contains a Gene Ontology enrichment bar chart of predicted targets that were negatively correlated with mir29b-3p.

To identify differentially expressed miRNA in patients with high CADI related to low CADI scores, the normalized data was first subjected surrogate variable analysis (SVA) to remove the variations between two groups FIGS. 8a and 8b). The two demographic parameters (gender and race) significantly contributed to data variation (FIG. 8a) and were removed after SVA correction (FIG. 8b). LIMMA test on SVA-adjusted data identified 24 differentially expressed miRNA (13 upregulated and 11 downregulated) at p value of 0.05 in high CADI patients (FIG. 2). The miRNA that were upregulated in high CADI group were hsa-miR-128, hsa-miR-182-5p, hsa-miR-151a-5p, hsa-miR-30c-5p, hsa-miR-302b-3p, hsa-miR-378e, hsa-miR-30b-5p, hsa-miR-23b-3p, hsa-miR-423-5p, hsa-miR-26a-5p, hsa-miR-423-5p, hsa-miR-26a-5p, hsa-miR-186-5p, hsa-miR-361-5p, and hsa-miR-22-3p. The miRNA that were downregulated in high CADI group were hsa-miR-7b-5p, hsa-miR-1991-5p, hsa-miR-22-3p, hsa-miR-7b-5p, hsa-miR-199a-5p, hsa-miR-7g-5p, hsa-miR-192-5p, hsa-miR-106b-5p, hsa-miR-15a-5p, hsa-miR-374a-5p, hsa-miR-126-3p, hsa-miR-29c-3p, hsa-miR-1226-3p, and hsa-miR-29b-3p. (FIG. 2) mir-128, an important miRNA with overexpression in many types of tumors, was the top upregulated miRNA in high CADI patients. mi29b-3p, known as a tumor suppressor, was the most significantly downregulated in high CADI patients. For better elucidation of the functional roles of these differentially expressed miRNA in progression of kidney fibrosis, the expression data of the miRNAs and their predicted targets from RNAseq on the same patients(N=96) was correlated and negatively corrected genes were identified for each miRNA. The data demonstrated an association of upregulation of mir-128 with gene down-regulation in immune response and cell death, and downregulation of mir-29b-3p with gene upregulation in transcription regulation, cell cycle and DNA damage repair through ATM signaling pathways (FIGS. 3a (mir-128) and 3b (mi29b-3p). These data suggested the important roles of microRNAs in regulating cellular proliferation in blood required to later development of kidney fibrosis.

miRNA Signature for Predicting Risk of Kidney Fibrosis in Renal Allograft Recipients This example demonstrates that certain miRNAs and miRNA sets can be used to predict a renal allograft recipient's risk of developing fibrosis of the allograft and allograft loss.

Figure 4A:
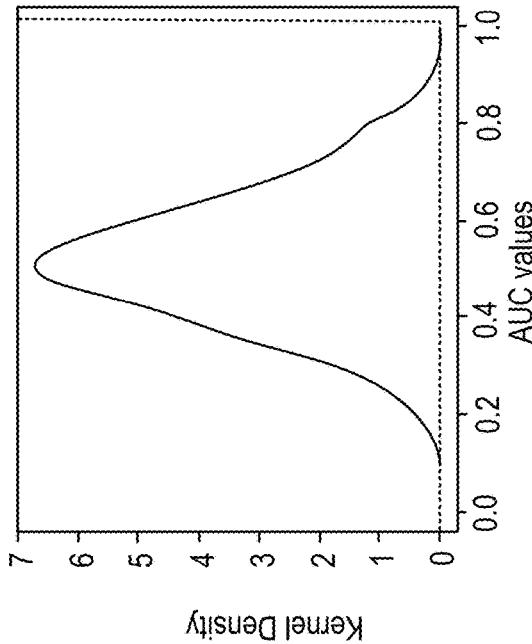
FIG. 4a contains a Prediction ROC curve of 4 miRNA prediction set on the training set.
Figure 4B:
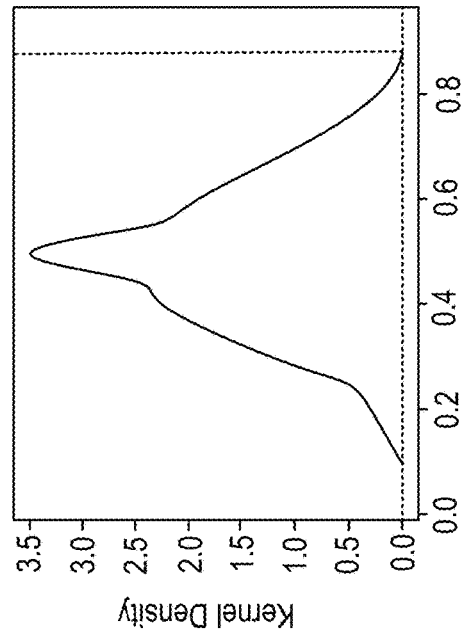
FIG. 4b depicts the distribution of AUCs on the training set derived from randomly selected 4 miRNA. The vertical red line denoted the position of the original AUC.
Figure 4C:
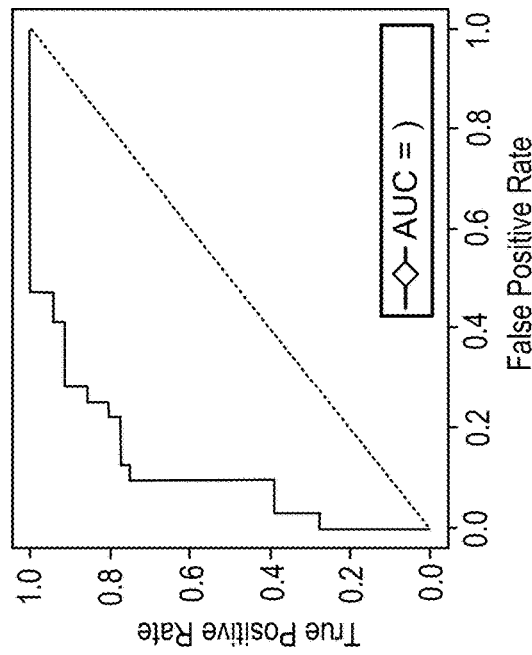
FIG. 4c contains a Prediction ROC curve of 4 miRNA prediction set on the testing set.
Figure 4D:
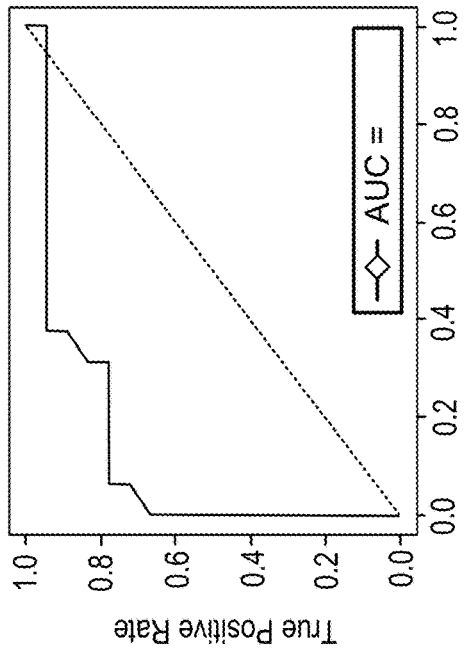
FIG. 4d depicts the distribution of AUCs on the testing set derived from randomly selected 4 miRNA. The vertical red line denoted the position of the original AUC.
Figure 9:
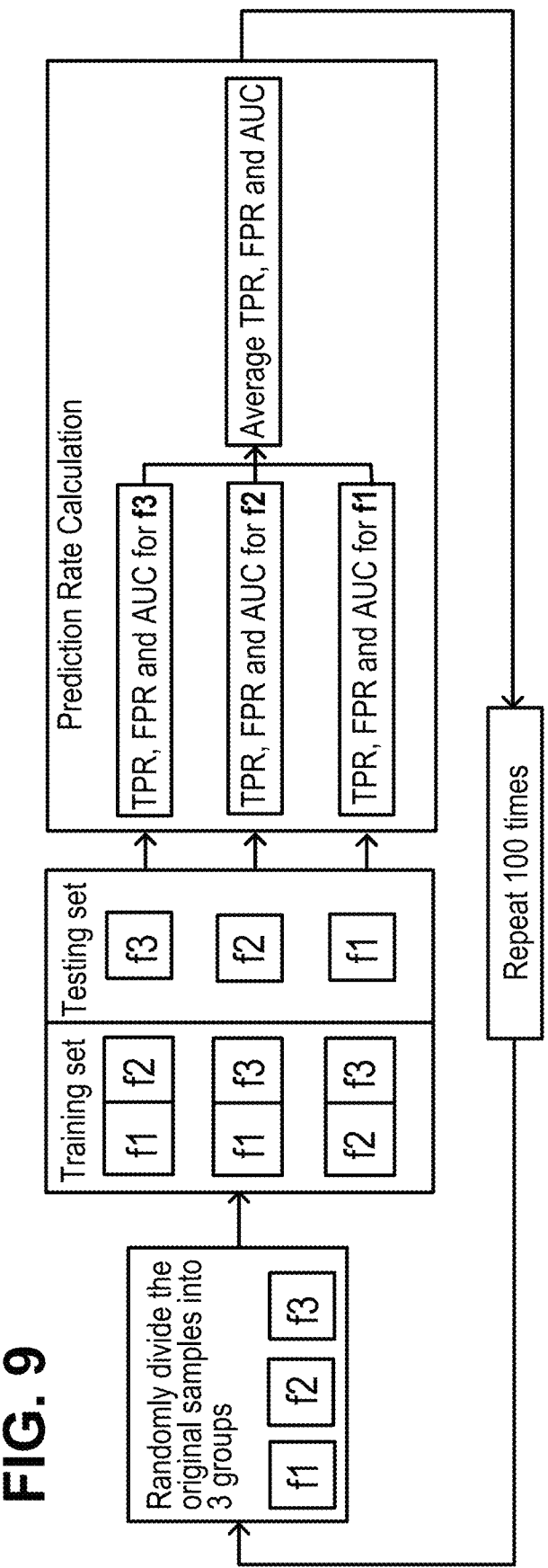
FIG. 9 is a schematic diagram illustrating the 3 fold cross validation steps on the training set with 100 iterations.

To identify a potential prognostic miRNA signature for prediction of development of kidney fibrosis and allograft loss, the 102 patients were divided into training set (N=68) and testing set (N=34). It was determined that 4 miRNAs (mir-128, mir-29b-3p, mir-302b-3p and mir-192-5p), which were derived from SVA-adjusted data of training set using penalized logistic regression model, were highly predictive. This 4-miRNA signature (mir-128, mir-29b-3p, mir-302b-3p and mir-192-5p), has a prediction AUC of 0.886 (FIG. 4a), which was higher than any AUCs derived from randomly selected 4 miRNAs (FIG. 4b). The 3-fold cross-validation with 100 iterations showed that the positive predictive value (PPV) and negative predictive value (NPV) were 0.87 and 0.66, respectively, suggesting the test is highly accurate. (FIG. 9)

Figure 10:
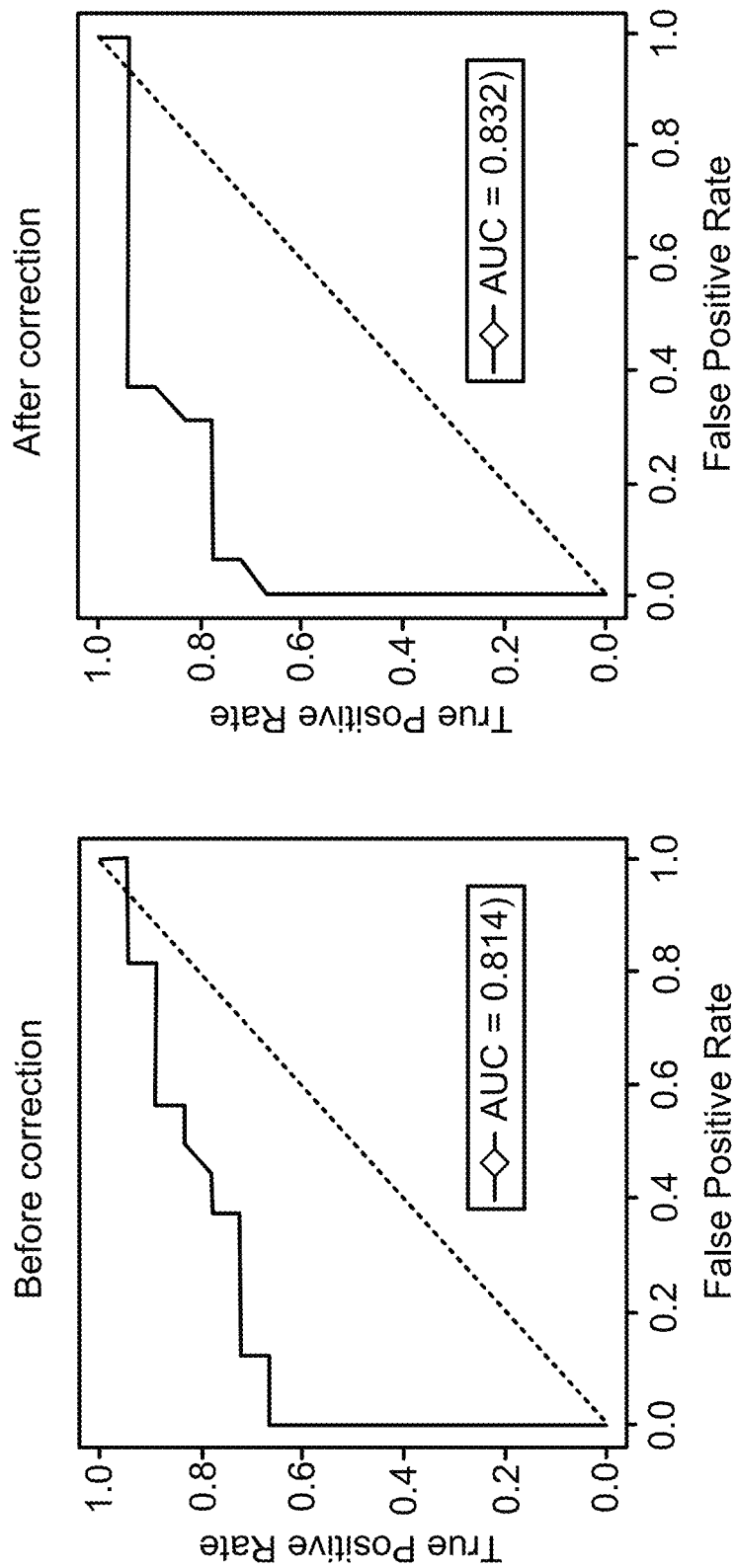
FIG. 10 contains graphs with the ROC curve before (left panel) and after (right panel) SVA correction. The true positive rage on the y-axis is plotted against the false positive rate on the x-axis.

After adjustment of each sample in the testing using the SVA model built on the training set, logistic regression model of 4 miRNAs from the training set was applied to predict the outcome of independent training set (N=34) with AUC 0.882 (FIG. 10), which is also higher than any AUCs derived from 4 randomly selected miRNAs.

Summary

The above study describes miRNA profiling using Nanostring technology on peripheral blood obtained 3 month post-transplant from a cohort of 102 kidney transplant patients from the Genomics of Chronic Allograft Rejection (GoCAR) study.

LIMMA analysis of miRNA expression profiles identified a set of 24 miRNAs significantly associated with m12 high CADI. Correlation of miRNA expression profiles with RNAseq gene expression profiles on the same patients (N=96) identified negatively correlated miRNA predicted targets and Gene Ontology enrichment further predicted the biological processes miRNAs might take part in. The mir-128, which is known to play roles in tumorigenesis, was the most significantly upregulated in high CADI patients and associated with genes in immune response and cell proliferation and apoptosis. The mir-29b-3p is the most downregulated in high CADI patients and associated with genes in transcription regulation, DNA repair pathways through in ATM pathway.

Further, the 102 patients were divided into training set (N=68) and testing set (N=34), the 4 miRNAs (mir-128, mir-29b-3p, mir-302b-3p and mir-192-5p) were derived from training set to predict high and low CADI patients with AUC 0.886 using penalized logistic regression model at probability score 0.5 cutoff 3-folder cross-validation indicated that the PPV and NPV were 0.87 and 0.66, respectively. These 4 miRNAs were further validated on independent training set (N=34) by the cutoff with AUC 0.882, sensitivity 83%, specificity 69%, PPV=75% and NPV=79%.

Prediction robustness of these 4 miRNAs (mir-128, mir-29b-3p, mir-302b-3p and mir-192-5p) was further assessed at a different CADI cutoff. At CADI cutoff 2 (low CADI<=2 and high CADI>2), 4 miRNAs remained significantly differentially expressed at p<0.05 between CADI low and high groups. Prediction AUC on training set (N=68) was 0.86 using penalized logistic regression model and the cutoff of probability score 0.75 was established at FPR<10%. These 4 miRNAs were validated on the testing set (N=34) by this cutoff with AUC 0.86, sensitivity 41%, specificity 100%, PPV=100% and NPV=63%. Compared to the prediction at CADI cutoff 1, the specificity and PPV were increased.

In summary, the miRNA profiling revealed a molecular signature from peripheral blood and the biological functions associated with future development of kidney allograft fibrosis and further identified a potential smaller set for prediction of kidney allograft fibrosis. This data suggests that peripheral miRNA profiling can be used as surveillance to stratify patients at risk for fibrosis and allograft loss, obviating the need for allograft biopsy, and identifying those who may benefit from early interventions to prevent chronic allograft loss.

While the combination of all four of mir-128, mir-29b-3p, mir-302b-3p and mir-192-5p was highly predictive of high risk (AUC of 0.886), subcombinations of the four miRNAs, as well as individual miRNAs were also predictive of high risk. For example, miR-128 had an AUC of 0.77, mir-29b-3p had an AUC of 0.65, but less accurate than prediction with 4 miRNAs.

A number of embodiments of the invention have been described. Nevertheless, it will be understood that various modifications may be made without departing from the spirit and scope of the invention. Accordingly, other embodiments are within the scope of the following claims.

It is further to be understood that all values are approximate, and are provided for description. patents, patent applications, publications, product descriptions, and protocols are cited throughout this application, the disclosures of which are incorporated herein by reference in their entireties for all purposes.

What is claimed is:

1. A method for identifying a renal allograft recipient at risk for developing fibrosis of the allograft the method comprising:
(a) determining the expression levels of four miRNAs in a blood sample from the recipient,
wherein the miRNAs are hsa-mir-128, hsa-mir-29b-3p, hsa-mir-302b-3p, and hsa-mir-192-5p; and
(b) identifying the recipient as being at risk for developing fibrosis of the allograft when the expression levels of said miRNAs hsa-miR-128 and hsa-miR-302b-3p are increased relative to a control level for each miRNA, and the expression levels of hsa-miR-29b-3p and hsa-miR-192-5p miRNAs are decreased relative to the control level for each miRNA.

2. The method of claim 1, wherein determining the expression levels comprise
synthesizing cDNA from miRNA isolated from said blood sample; and
determining the expression levels of miRNAs hsa-mir-128, hsa-mir-29b-3p, hsa-mir-302b-3p, and hsa-mir-192-5p in said sample.

3. The method of claim 2, wherein identifying the recipient's risk comprises applying the expression levels determined in the recipient's sample to a penalized logistic regression fitting model.

4. The method of claim 3, wherein the penalized logistic regression fitting model utilizes the formula:

$$\log\frac{p(x)}{1-p(x)} = \beta^*_{0+}\beta^*_1 g_1 + \beta^*_i g_i + \ldots + \beta^*_4 g_4$$

where (p(x) is the probability of developing fibrosis, $\beta^*_i$ is penalized coefficiency and $g_i$ is the expression value of miRNA i.

5. The method of claim 1, further comprising administering an anti-rejection drug to the allograft recipient identified as being at high risk for developing fibrosis of the allograft.

6. The method of claim 5, wherein the anti-rejection drug is cyclosporine.

7. The method of claim 5, wherein the anti-rejection drug is an immunosuppressive or anti-proliferative agent.

8. The method of claim 7, wherein the immunosuppressive agent is a member selected from the group consisting of a mycophenolate mofetil (MMF), sirolimus, prednisone, Mycophenolate Sodium and Azathioprine.

9. The method of claim 1, further comprising administering an anti-fibrosis drug to the allograft recipient identified as being at high risk for developing fibrosis of the allograft.

10. The method of claim 9, wherein the anti-fibrosis drug is selected from the group consisting of Pirfenidone, relaxin, Bone morphogenetic protein 7 (BMP-7) and Hepatic growth factor (HGF) 6.

11. The method of claim 2, wherein determining the expression levels of miRNAs hsa-mir-128, hsa-mir-29b-3p, hsa-mir-302b-3p, and hsa-mir-192-5p comprises performing an assay selected from the group consisting of qPCR analysis, microarray, and Nanostring analysis.

12. The method of claim 11, further comprising modifying the immunosuppression regimen of an allograft recipient identified as being at high risk for fibrosis of the allograft.

13. The method of claim 12, wherein modifying the immunosuppression regimen comprises administering to the recipient an anti-rejection drug selected from the group consisting of Belatacept, rapamycin and Mycophenolate Mofetil.

14. The method of claim 12, wherein modifying the immunosuppression regimen comprises administering to the recipient an anti-fibrosis drug selected from the group consisting of Pirfenidone, relaxin, Bone morphogenetic protein 7 (BMP-7) and Hepatic growth factor (HGF) 6.

15. The method of claim 1 further comprising identifying the recipient as being at low risk for developing fibrosis of the allograft when the expression levels of miRNAs hsa-miR-128 and hsa-miR-302b-3p are decreased relative to the control level for each miRNA, and the expression levels of hsa-miR-29b-3p and hsa-miR-192-5p are increased relative to the control level for each miRNA.

16. The method of claim 15, wherein identifying the recipient comprises calculating the recipient's risk by applying the expression levels determined in the recipient's sample to a penalized logistic regression fitting model.

17. The method of claim 16, further comprising calculating the probability score of fibrosis risk for said recipient using the equation:

$\log(p(x))/(1-p(x)) = \beta^*0 + \beta^*1 g1 + \beta^* igi + \ldots + \beta^*4 g4$ where (p(x) is the probability of developing fibrosis, $\beta^*i$ is penalized coefficiency and gi is the expression value of miRNA i.

18. The method of claim 17 wherein determining the expression levels of miRNAs hsa-mir-128, hsa-mir-29b-3p, hsa-mir-302b-3p, and hsa-mir-192-5p comprises performing an assay selected from the group consisting of qPCR analysis, microarray, and Nanostring analysis.

19. The method of claim 18, further comprising modifying the immunosuppression regimen of the allograft recipient identified as being at low risk for fibrosis of the allograft.

20. The method of claim 19 wherein modifying the immunosuppression regimen comprises administering to the recipient an anti-rejection drug selected from the group consisting of Belatacept, rapamycin and Mycophenolate Mofetil.

21. The method of claim 20, wherein modifying the immunosuppression regimen comprises administering to the recipient an anti-fibrosis drug selected from the group consisting of Pirfenidone, relaxin, Bone morphogenetic protein 7 (BMP-7) and Hepatic growth factor (HGF) 6.

22. A method for identifying a renal allograft recipient at risk for allograft loss comprising the steps of
determining the expression levels of miRNAs hsa-mir-128, hsa-mir-29b-3p, hsa-mir-302b-3p, and hsa-mir-192-5p in a blood sample obtained from said recipient, and
identifying the recipient as being at risk for allograft loss when the expression levels of said miRNAs are altered relative to a control level for each-miRNA.

23. The method of claim 22 further comprising identifying the recipient as being at high risk for allograft loss when the expression levels of miRNAs hsa-miR-128 and hsa-miR-302b-3p are increased relative to the control level for each miRNA, and the expression levels of hsa-miR-29b-3p and hsa-miR-192-5p are decreased relative to the control level for each miRNA.

24. The method of claim 23, further comprising administering an anti-rejection drug to the allograft recipient-identified as being at high risk for allograft loss.

25. The method of claim 24, wherein the anti-rejection drug is an immunosuppressive or anti-proliferative agent.

26. The method of claim 25 further comprising identifying the recipient as being at low risk for allograft loss when the expression levels of miRNAs hsa-miR-128 and hsa-miR-302b-3p are decreased relative to the control level for each miRNA, and the expression levels of hsa-miR-29b-3p and hsa-miR-192-5p are increased relative to the control level for each miRNA.

27. The method of claim 26, further comprising modifying the immunosuppression regimen of an allograft recipient identified as being at low risk for allograft loss.

28. The method of claim 27 wherein modifying the immunosuppression regimen comprises administering to the recipient an anti-rejection drug selected from the group consisting of Belatacept, rapamycin and Mycophenolate Mofetil.

* * * * *